(12) United States Patent
Yan et al.

(10) Patent No.: US 12,234,275 B2
(45) Date of Patent: Feb. 25, 2025

(54) ANTI-CD19 CAR-T CELL

(71) Applicant: BEIJING MARINO BIOTECHNOLOGY PTY LTD., Beijing (CN)

(72) Inventors: Yongchao Yan, Beijing (CN); Yilin Zhu, Beijing (CN); Siyi Chen, Beijing (CN)

(73) Assignee: BEIJING MARINO BIOTECHNOLOGY PTY LTD., Beijing (CN)

( * ) Notice: Subject to any disclaimer, the term of this patent is extended or adjusted under 35 U.S.C. 154(b) by 1101 days.

(21) Appl. No.: 17/101,785

(22) Filed: Nov. 23, 2020

(65) Prior Publication Data
US 2021/0196756 A1 Jul. 1, 2021

Related U.S. Application Data

(63) Continuation of application No. PCT/CN2018/111640, filed on Oct. 24, 2018.

(30) Foreign Application Priority Data

May 24, 2018 (CN) ............................ 201810509014

(51) Int. Cl.
| | | |
|---|---|---|
| A61K 35/17 | (2015.01) | |
| A61K 39/00 | (2006.01) | |
| C07K 14/705 | (2006.01) | |
| C07K 14/71 | (2006.01) | |
| C07K 16/28 | (2006.01) | |
| C12N 5/0783 | (2010.01) | |

(52) U.S. Cl.
CPC .... *C07K 14/70517* (2013.01); *A61K 39/4611* (2023.05); *A61K 39/4631* (2023.05); *A61K 39/464404* (2023.05); *A61K 39/464412* (2023.05); *C07K 14/71* (2013.01); *C07K 16/2803* (2013.01); *C12N 5/0636* (2013.01); *C12N 5/0638* (2013.01); *A61K 2039/505* (2013.01)

(58) Field of Classification Search
CPC ..................................................... A61K 35/17
See application file for complete search history.

(56) References Cited

FOREIGN PATENT DOCUMENTS

| | | |
|---|---|---|
| CN | 106467906 | 3/2017 |
| CN | 106967684 | 7/2017 |
| CN | 107034193 | 8/2017 |
| CN | 107603995 | 1/2018 |
| CN | 107880128 | 4/2018 |
| CN | 108070607 | 5/2018 |
| CN | 108070608 | 5/2018 |
| WO | 2016090470 A1 | 6/2016 |
| WO | 2017028374 A1 | 2/2017 |
| WO | 2017120997 A1 | 7/2017 |

OTHER PUBLICATIONS

NCBI Printout for the CD8 alpha isoform 1 amino acid sequence (4 pages). (Year: 2024).*
NCBI Printout for the CD8 alpha isoform 2 amino acid sequence (4 pages). (Year: 2024).*
UPO, Notice of Reasons for Refusal issued for JP Application No. 2021-515259, Dec. 7, 2021.
Epo, Extended European Search Report issued for EP Application No. 18920160.1, Feb. 7, 2022.
Milone et al., Molecular Therapy, "Chimeric Receptors Containing CD137 Signal Transduction Domains Mediate Enhanced Survival of T Cells and Increased Antileukemic Efficacy In Vivo", vol. 17, No. 8, Aug. 2009, pp. 1453-1464.
Albanza et al., Molecular Therapy, "Function of Novel Anti-CD19 Chimeric Antigen Receptors with Human Variable Regions is Affected by Hing and Transmembrane Domains", vol. 25, No. 11, Nov. 2017, pp. 2452-2465.
Zhitao et al., "Application Progress of Chimeric Antigen Receptor T Cell in Treatment of B Cell Lymphoma and Existing Problems", vol. 12, No. 5, 2017, pp. 318-323.
WIPO, ISR for PCT/CN2018/111640, Feb. 11, 2019.
SIPO, First Office Action for CN Application No. 201810509014.4, Sep. 3, 2020.
Paszkiewicz et al., "Targeted antibody-mediated depletion of murine CD19 CAR T cells permanently reverses B cell aplasia," The Journal of Clinical Investigation, Nov. 2016, vol. 126, No. 11, pp. 4262-4272.

* cited by examiner

*Primary Examiner* — Anoop K Singh
*Assistant Examiner* — David A Montanari
(74) *Attorney, Agent, or Firm* — Hodgson Russ LLP

(57) ABSTRACT

A chimeric antigen receptor is provided, including an extracellular segment, including a single-chain antibody region binding to an antigen human CD19 and a hinge region, a trans-membrane segment, including a trans-membrane domain of human CD8α linked to the hinge region of the extracellular segment and embedded in cell membrane of T lymphocyte, and an intracellular segment, including an intracellular domain of human CD8α, an intracellular domain of molecule 4-1BB and an intracellular domain of CD3 ζ chain. The single-chain antibody region includes a heavy-chain variable region and a light-chain variable region of the single-chain antibody, the hinge region includes an extracellular domain of human CD8 alpha (CD8α) of 55 amino acid residues and three alanine residues (AAA) located at the N-terminal of the extracellular domain of human CD8α, and the intracellular domain of human CD8α includes seven amino acid residues and linked to the trans-membrane domain of human CD8α.

14 Claims, 3 Drawing Sheets
Specification includes a Sequence Listing.

A

B

ANTI-CD19 CAR-T CELL

CROSS-REFERENCE TO RELATED APPLICATION

This application is a continuation application of PCT Application No. PCT/CN2018/111640 filed on Oct. 24, 2018, and claims a priority to and benefits of Chinese Patent Application No. 201810509014.4 filed on May 24, 2018, the entire contents of which are incorporated herein by reference.

FIELD

The present disclosure relates to the field of biomedicine, particularly relates to an anti-CD19 chimeric antigen receptor, a T lymphocyte, a lentiviruse, a transgenic lymphocyte, a construct, a therapeutic composition for treating a cancer, and a method for improving safety of lymphocyte therapy.

BACKGROUND

Chimeric antigen receptor (CAR)-T cell therapy is a kind of immunotherapy that can effectively treat malignant tumors, especially hematological tumors. The chimeric antigen receptor (CAR) is a fusion protein including a single-chain antibody region and an intracellular T cell signal transduction region, in which the single-chain antibody region and the intracellular T cell signal transduction region are connected by hinge region and trans-membrane segment of the chimeric antigen receptor, and the hinge region and the trans-membrane segment of CAR may be essential for the expression of the chimeric antigen receptor by T cells. Recent clinical trials showed that the anti-CD19 CAR-T cell therapy has greatly alleviated symptoms of patients with advanced B-cell malignancy. Despite exhibiting a strong therapeutic efficacy on treating acute leukemia and lymphoma evidenced by numerous clinical tests, the anti-CD19 CAR-T cell therapy still has severe side effects, including severe cytokine release syndrome (CRS) and neurotoxicity in brain, which can endanger the life of patients.

Two autologous anti-CD19 CAR-T cell therapeutic products, CTL019 (Kymriah) and KTE-C19 (Yescarta), have been approved by Food and Drug Administration (FDA) for the treatment of relapsed or refractory leukemia or lymphoma. Specifically, anti-CD19 CAR-T cell therapy (Kymriah) by NOVARTIS Company, also known as CTL019, was approved for the treatment of acute lymphoblastic leukemia (ALL) in August 2017, which is the first CAR-T therapy approved in history. According to the data of CTL019 on treating diffuse large B cell lymphoma (DLBCL) in global pivotal phase 2 clinical trial (Juliet trial) issued by NOVARTIS in the abstract of the annual meeting of the American Society of Hematology (ASH) in December 2017, researchers assessed the therapeutic effect of CTL019 on relapsed or refractory DLBCL patients by administration of a single dose of CTL019 to 99 patients, with results showing 53.1% of best overall response rate (ORR) and 39.5% of complete response rate (CR), along with 86% of patients suffering from grade 3 or 4 side effects and 58% of patients suffering from cytokine release syndrome.

Researchers have found that the anti-CD19 CAR-T cell therapy often causes severe toxic reactions despite having excellent efficacy, including severe cytokine release syndrome and neurotoxicity, during which the main cause of the severe cytokine release syndrome and neurotoxicity is the rapid cell proliferation of CD19 CAR-T cells and thus resulting in excessive release of inflammatory cytokines in patients. Therefore, improving the safety of anti-CD19 CAR-T cell therapy and reducing its side effects is the key to the widespread and routine application of anti-CD19 CAR-T cell therapy in the treatment of leukemia and lymphoma in the future.

SUMMARY

This application is based on the discovery of present inventors in solving the following issues and facts.

CTL019 (Kymriah) of NOVARTIS is a fusion protein of anti-CD19-BBz CAR, comprising an extracellular anti-CD19 FMC63 single-chain antibody region (scFv) and an intracellular co-stimulatory factor 4-1BB region and T receptor CD3z signaling domain, in which the extracellular anti-CD19 FMC63 single-chain antibody region (scFv) and the intracellular co-stimulatory factor 4-1BB region and T receptor CD3z signaling domain are linked with the hinge region and trans-membrane domain of CD8α (Imai, C. et al. Leukemia. 2004; 18:676-684; Milone M C, et al. Mol Ther. 2009; 17:1453-64). However, CTL019 (Kymriah) generates severe side effects related to severe cytokine release syndrome and neurotoxicity caused by the rapid cell proliferation of CD19 CAR-T cells and thus resulting in excessive release of inflammatory cytokines in patients.

The present inventors have found that the amino acid sequence of the hinge region, the trans-membrane segment and the intracellular region would affect the spatial configuration of CAR molecule, thus in turn affect the formation of dimer and multimer, and further affect the binding with downstream signaling molecules, thereby affecting activation of lymphocytes and production of cytokines.

Based on the above discovery, the inventors modified the hinge region, the trans-membrane segment and the intracellular region of the CD19-BBz CAR fusion protein of the prior art, thus obtained a modified CD19-BBz CAR fusion protein having improved spatial configuration and dimer which affect binding with downstream signaling molecules. The inventors surprisingly discovered that the lymphocytes containing the modified CD19-BBz CAR fusion protein have reduced cell proliferation and thus generate decreased cytokines, with strong but safer tumor killing ability. The present application aims to solve at least one of the technical problems of the prior art to a certain degree.

In a first aspect, the present disclosure in embodiments provides a chimeric antigen receptor.

In embodiments of the present disclosure, the chimeric antigen receptor comprises:

an extracellular segment, comprising a single-chain antibody region specifically binding to an antigen human CD19 and a hinge region, wherein the single-chain antibody region comprises a heavy chain variable region and a light chain variable region of the single-chain antibody, and the hinge region comprises an extracellular domain of human CD8 alpha (CD8α) of 55 amino acid residues and three alanine residues (AAA) located at the N-terminal of the extracellular domain of human CD8α, a trans-membrane segment, comprising a trans-membrane domain of human CD8α linked to the hinge region of the extracellular segment and embedded in cell membrane of T lymphocyte, and an intracellular segment, comprising an intracellular domain of human CD8α, an intracellular domain of molecule 4-1BB and an intracellular domain of CD3 ζ chain, wherein the intracellular domain of human CD8α comprises seven amino acid residues and linked to the trans-membrane domain of human CD8α.

Compared to the prior art, the modified chimeric antigen receptor according to embodiments of the present disclosure has improved spatial configuration, thus the T lymphocytes expressing the modified chimeric antigen receptor have strong tumor killing ability while having reduced cell proliferation and decreased production of cytokines, thereby reducing the side effects related to severe cytokine release syndrome and neurotoxicity.

In embodiments of the present disclosure, the T lymphocytes as described above may further comprise at least one of the following additional technical features.

In embodiments of the present disclosure, the extracellular domain of human CD8 comprises the amino acid sequence shown in SEQ ID NO: 1.

(SEQ ID NO: 1)
FVPVFLPAKPTTTPAPRPPTPAPTIASQPLSLRPEACRPAAGGAVHTRG
LDFACD

In embodiments of the present disclosure, the trans-membrane domain of human CD8α comprises the amino acid sequence shown in SEQ ID NO: 2.

(SEQ ID NO: 2)
IYIWAPLAGTCGVLLLSLVIT

In embodiments of the present disclosure, the intracellular domain of human CD8α comprises the amino acid sequence shown in SEQ ID NO: 3.

(SEQ ID NO: 3)
LYCNHRN

In embodiments of the present disclosure, the extracellular segment comprises the amino acid sequence shown in SEQ ID NO: 4.

(SEQ ID NO: 4)
MLLLVTSLLLCELPHPAFLLIPDIQMTQTTSSLSASLGDRVTISCRASQ

DISKYLNWYQQKPDGTVKLLIYHTSRLHSGVPSRFSGSGSGTDYSLTIS

NLEQEDIATYFCQQGNTLPYTFGGGTKLEITGSTSGSGKPGSGEGSTKG

EVKLQESGPGLVAPSQSLSVTCTVSGVSLPDYGVSWIRQPPRKGLEWLG

VIWGSETTYYNSALKSRLTIIKDNSKSQVFLKMNSLQTDDTAIYYCAKH

YYYGGSYAMDYWGQGTSVTVSSAAAFVPVFLPAKPTTTPAPRPPTPAPT

IASQPLSLRPEACRPAAGGAVHTRGLDFACD

In embodiments of the present disclosure, the trans-membrane segment comprises the amino acid sequence shown in SEQ ID NO: 5.

(SEQ ID NO: 5)
IYIWAPLAGTCGVLLLSLVIT

In embodiments of the present disclosure, the intracellular segment comprises the amino acid sequence shown in SEQ ID NO: 6.

(SEQ ID NO: 6)
LYCNHRNKRGRKKLLYIFKQPFMRPVQTTQEEDGCSCRFPEEEEGGCEL

RVKFSRSADAPAYQQGQNQLYNELNLGRREEYDVLDKRRGRDPEMGGKP

RRKNPQEGLYNELQKDKMAEAYSEIGMKGERRRGKGHDGLYQGLSTATK

DTYDALHMQALPPR

In embodiments of the present disclosure, the hinge region comprises the amino acid sequence shown in SEQ ID NO: 7.

(SEQ ID NO: 7)
AAAFVPVFLPAKPTTTPAPRPPTPAPTIASQPLSLRPEACRPAAGGAVH
TRGLDFACD

According to the modified chimeric antigen receptor comprising the extracellular segment, the trans-membrane segment and the intracellular segment of the amino acid sequences shown in the above, the T lymphocytes expressing the modified chimeric antigen receptor have reduced cell proliferation and decreased but safer production of cytokines, thereby obtaining a safer tumor killing ability.

In a second aspect, the present disclosure in embodiments provides a T lymphocyte. According to embodiments of the present disclosure, the T lymphocyte expresses a non-functional epidermal growth factor receptor (EGFR) and the anti-CD19 chimeric antigen receptor as defined above. The non-functional EGFR lacks the N-terminal ligand binding region and the activity of intracellular receptor tyrosine kinase, but includes the trans-membrane region of wild-type EGFR and the complete amino acid sequence that binds to anti-EGFR antibody, thus the non-functional EGFR can be used as a suicide mark for lymphocytes. Therefore, the T lymphocytes in embodiments of the present disclosure have a targeted killing ability on tumor cells highly expressing CD19, with moderate cell proliferation and decreased but safer production of cytokines, thus exhibiting safe tumor killing properties. The T lymphocytes according to embodiments of the present disclosure as described above can be a modified anti-CD19 CAR-T cells which have safer antitumor activity compared to the prior art.

In a third aspect, the present disclosure in embodiments provides a lentivirus. According to embodiments of the present disclosure, the lentivirus carries a first nucleic acid molecule encoding a chimeric antigen receptor, wherein the chimeric antigen receptor comprises the amino acid sequence shown in SEQ ID NO: 8 and the first nucleic acid molecule comprises the nucleotide sequence shown in SEQ ID NO: 9, and a second nucleic acid molecule encoding a non-functional EGFR, wherein the non-functional EGFR comprises the amino acid sequence shown in SEQ ID NO: 10 and the second nucleic acid molecule comprises the nucleotide sequence shown in SEQ ID NO: 11.

(SEQ ID NO: 8)
MLLLVTSLLLCELPHPAFLLIPDIQMTQTTSSLSASLGDRVTISCRASQ

DISKYLNWYQQKPDGTVKLLIYHTSRLHSGVPSRFSGSGSGTDYSLTIS

NLEQEDIATYFCQQGNTLPYTFGGGTKLEITGSTSGSGKPGSGEGSTKG

EVKLQESGPGLVAPSQSLSVTCTVSGVSLPDYGVSWIRQPPRKGLEWLG

VIWGSETTYYNSALKSRLTIIKDNSKSQVFLKMNSLQTDDTAIYYCAKH

YYYGGSYAMDYWGQGTSVTVSSAAAFVPVFLPAKPTTTPAPRPPTPAPT

-continued
IASQPLSLRPEACRPAAGGAVHTRGLDFACDIYIWAPLAGTCGVLLLSL
VITLYCNHRNKRGRKKLLYIFKQPFMRPVQTTQEEDGCSCRFPEEEEGG
CELRVKFSRSADAPAYQQGQNQLYNELNLGRREEYDVLDKRRGRDPEMG
GKPRRKNPQEGLYNELQKDKMAEAYSEIGMKGERRRGKGHDGLYQGLST
ATKDTYDALHMQALPPR (SEQ ID NO: 9)
ATGCTTCTCCTGGTGACAAGCCTTCTGCTCTGTGAGTTACCACACCCAG
CATTCCTCCTGATCCCAGACATCCAGATGACACAGACTACATCCTCCCT
GTCTGCCTCTCTGGGAGACAGAGTCACCATCAGTTGCAGGGCAAGTCAG
GACATTAGTAAATATTTAAATTGGTATCAGCAGAAACCAGATGGAACTG
TTAAACTCCTGATCTACCATACATCAAGATTACACTCAGGAGTCCCATC
AAGGTTCAGTGGCAGTGGGTCTGGAACAGATTATTCTCTCACCATTAGC
AACCTGGAGCAAGAAGATATTGCCACTTACTTTTGCCAACAGGGTAATA
CGCTTCCGTACACGTTCGGAGGGGGGACTAAGTTGGAAATAACAGGCTC
CACCTCTGGATCCGGCAAGCCCGGATCTGGCGAGGGATCCACCAAGGGC
GAGGTGAAACTGCAGGAGTCAGGACCTGGCCTGGTGGCGCCCTCACAGA
GCCTGTCCGTCACATGCACTGTCTCAGGGGTCTCATTACCCGACTATGG
TGTAAGCTGGATTCGCCAGCCTCCACGAAAGGGTCTGGAGTGGCTGGGA
GTAATATGGGGTAGTGAAACCACATACTATAATTCAGCTCTCAAATCCA
GACTGACCATCATCAAGGACAACTCCAAGAGCCAAGTTTTCTTAAAAAT
GAACAGTCTGCAAACTGATGACACAGCCATTTACTACTGTGCCAAACAT
TATTACTACGGTGGTAGCTATGCTATGGACTACTGGGGTCAAGGAACCT
CAGTCACCGTCTCCTCAGCGGCCGCATTCGTGCCGGTCTTCCTGCCAGC
GAAGCCCACCACGACGCCAGCGCCGCGACCACCAACACCGGCGCCCACC
ATCGCGTCGCAGCCCCTGTCCCTGCGCCCAGAGGCGTGCCGGCCAGCGG
CGGGGGGCGCAGTGCACACGAGGGGGCTGGACTTCGCCTGTGATATCTA
CATCTGGGCGCCCTTGGCCGGGACTTGTGGGGTCCTTCTCCTGTCACTG
GTTATCACCCTTTACTGCAACCACAGGAACAAACGGGGCAGAAAGAAAC
TCCTGTATATATTCAAACAACCATTTATGAGACCAGTACAAACTACTCA
AGAGGAAGATGGCTGTAGCTGCCGATTTCCAGAAGAAGAAGAAGGAGGA
TGTGAACTGAGAGTGAAGTTCAGCAGGAGCGCAGACGCCCCCGCGTACC
AGCAGGGCCAGAACCAGCTCTATAACGAGCTCAATCTAGGACGAAGAGA
GGAGTACGATGTTTTGGACAAGAGACGTGGCCGGGACCCTGAGATGGGG
GGAAAGCCGAGAAGGAAGAACCCTCAGGAAGGCCTGTACAATGAACTGC
AGAAAGATAAGATGGCGGAGGCCTACAGTGAGATTGGGATGAAAGGCGA
GCGCCGGAGGGGCAAGGGGCACGATGGCCTTTACCAGGGTCTCAGTACA
GCCACCAAGGACACCTACGACGCCCTTCACATGCAGGCCCTGCCCCCTC
GCTAA (SEQ ID NO: 10)
MALPVTALLLPLALLLHAARPGSRKVCNGIGIGEFKDSLSINATNIKHF
KNCTSISGDLHILPVAFRGDSFTHTPPLDPQELDILKTVKEITGFLLIQ
AWPENRTDLHAFENLEIIRGRTKQHGQFSLAVVSLNITSLGLRSLKEIS
DGDVIISGNKNLCYANTINWKKLFGTSGQKTKIISNRGENSCKATGQVC
HALCSPEGCWGPEPRDCVSCRNVSRGRECVDKCNLLEGEPREFVENSEC
IQCHPECLPQAMNITCTGRGPDNCIQCAHYIDGPHCVKTCPAGVMGENN
TLVWKYADAGHVCHLCHPNCTYGCTGPGLEGCPTNGPKIPSIATGMVGA
LLLLLVVALGIGLFMRR (SEQ ID NO: 11)
ATGGCTCTGCCCGTCACCGCTCTGCTGCTGCCTCTGGCTCTGCTGCTGC
ACGCCGCACGCCCTGGGAGTCGCAAAGTCTGTAATGGGATCGGCATCGG
CGAGTTCAAGGACAGCCTGTCCATCAACGCCACCAATATCAAGCACTTT
AAGAATTGCACATCTATCAGCGGCGACCTGCACATCCTGCCAGTGGCCT
TCCGGGGCGATTCTTTTACCCACACACCCCCTCTGGACCCTCAGGAGCT
GGATATCCTGAAGACCGTGAAGGAGATCACAGGCTTCCTGCTGATCCAG
GCCTGGCCTGAGAACAGAACCGATCTGCACGCCTTTGAGAATCTGGAGA
TCATCCGGGGCAGAACAAAGCAGCACGGCCAGTTCTCCCTGGCCGTGGT
GTCTCTGAACATCACCAGCCTGGGCCTGAGGTCCCTGAAGGAGATCTCT
GACGGCGATGTGATCATCTCCGGCAACAAGAACCTGTGCTACGCCAACA
CAATCAATTGGAAGAAGCTGTTTGGCACCTCTGGCCAGAAGACAAAGAT
CATCTCTAACCGGGGCGAGAATAGCTGCAAGGCAACCGGACAGGTGTGC
CACGCACTGTGCAGCCCAGAGGGATGTTGGGGCCCAGAGCCACGGGACT
GCGTGAGCTGTAGAAACGTGTCCAGGGGCCGCGAGTGCGTGGATAAGTG
TAATCTGCTGGAGGGCGAGCCAAGGGAGTTCGTGGAGAACTCCGAGTGC
ATCCAGTGTCACCCCGAGTGCCTGCCTCAGGCCATGAACATCACCTGTA
CAGGCCGCGGCCCCGACAATTGCATCCAGTGTGCCCACTATATCGATGG
CCCTCACTGCGTGAAGACCTGTCCAGCCGGCGTGATGGGCGAGAACAAT
ACACTGGTGTGGAAGTACGCAGACGCAGGACACGTGTGCCACCTGTGCC
ACCCCAATTGCACCTATGGCTGTACAGGACCAGGCCTGGAGGGATGCCC
AACCAACGGCCCTAAGATCCCAAGCATCGCCACAGGCATGGTGGGGGCA
CTGCTGCTGCTGGTGGTGGCTCTGGGGATTGGGCTGTTTATGAGAA
GGTAA In embodiments of the present disclosure, a transgenic lymphocyte is obtained by transducing the lentivirus into a lymphocyte, which has a targeted killing ability on tumor cells, especially on tumor cells highly expressing CD19, with moderate cell proliferation and decreased but safer production of cytokines, thus showing slow and lasting tumor killing properties. The obtained modified anti-CD19 CAR cells have safer anti-tumor activity.

In a fourth aspect, the present disclosure in embodiments provides a lentivirus. According to embodiments of the present disclosure, the lentivirus comprises the nucleotide sequence shown in SEQ ID NO: 12.

(SEQ ID NO: 12)
ATGCTTCTCCTGGTGACAAGCCTTCTGCTCTGTGAGTTACCACACCCAG
CATTCCTCCTGATCCCAGACATCCAGATGACACAGACTACATCCTCCCT

-continued
GTCTGCCTCTCTGGGAGACAGAGTCACCATCAGTTGCAGGGCAAGTCAG

GACATTAGTAAATATTTAAATTGGTATCAGCAGAAACCAGATGGAACTG

TTAAACTCCTGATCTACCATACATCAAGATTACACTCAGGAGTCCCATC

AAGGTTCAGTGGCAGTGGGTCTGGAACAGATTATTCTCTCACCATTAGC

AACCTGGAGCAAGAAGATATTGCCACTTACTTTTGCCAACAGGGTAATA

CGCTTCCGTACACGTTCGGAGGGGGGACTAAGTTGGAAATAACAGGCTC

CACCTCTGGATCCGGCAAGCCCGGATCTGGCGAGGGATCCACCAAGGGC

GAGGTGAAACTGCAGGAGTCAGGACCTGGCCTGGTGGCGCCCTCACAGA

GCCTGTCCGTCACATGCACTGTCTCAGGGGTCTCATTACCCGACTATGG

TGTAAGCTGGATTCGCCAGCCTCCACGAAAGGGTCTGGAGTGGCTGGGA

GTAATATGGGGTAGTGAAACCACATACTATAATTCAGCTCTCAAATCCA

GACTGACCATCATCAAGGACAACTCCAAGAGCCAAGTTTTCTTAAAAAT

GAACAGTCTGCAAACTGATGACACAGCCATTTACTACTGTGCCAAACAT

TATTACTACGGTGGTAGCTATGCTATGGACTACTGGGGTCAAGGAACCT

CAGTCACCGTCTCCTCAGCGGCCGCATTCGTGCCGGTCTTCCTGCCAGC

GAAGCCCACCACGACGCCAGCGCCGCGACCACCAACACCGGCGCCCACC

ATCGCGTCGCAGCCCCTGTCCCTGCGCCCAGAGGCGTGCCGGCCAGCGG

CGGGGGCGCAGTGCACACGAGGGGGCTGGACTTCGCCTGTGATATCTA

CATCTGGGCGCCCTTGGCCGGGACTTGTGGGGTCCTTCTCCTGTCACTG

GTTATCACCCTTTACTGCAACCACAGGAACAAACGGGGCAGAAAGAAAC

TCCTGTATATATTCAAACAACCATTTATGAGACCAGTACAAACTACTCA

AGAGGAAGATGGCTGTAGCTGCCGATTTCCAGAAGAAGAAGAAGGAGGA

TGTGAACTGAGAGTGAAGTTCAGCAGGAGCGCAGACGCCCCCGCGTACC

AGCAGGGCCAGAACCAGCTCTATAACGAGCTCAATCTAGGACGAAGAGA

GGAGTACGATGTTTTGGACAAGAGACGTGGCCGGGACCCTGAGATGGGG

GGAAAGCCGAGAAGGAAGAACCCTCAGGAAGGCCTGTACAATGAACTGC

AGAAAGATAAGATGGCGGAGGCCTACAGTGAGATTGGGATGAAAGGCGA

GCGCCGGAGGGGCAAGGGGCACGATGGCCTTTACCAGGGTCTCAGTACA

GCCACCAAGGACACCTACGACGCCCTTCACATGCAGGCCCTGCCCCCTC

GCTAATCCTACTGCGTCGACTTCGAATTTAAATCGGATCCGCGGCCGCG

CCCCTCTCCCTCCCCCCCCCCTAACGTTACTGGCCGAAGCCGCTTGGAA

TAAGGCCGGTGTGCGTTTGTCTATATGTTATTTTCCACCATATTGCCGT

CTTTTGGCAATGTGAGGGCCCGGAAACCTGGCCCTGTCTTCTTGACGAG

CATTCCTAGGGGTCTTTCCCCTCTCGCCAAAGGAATGCAAGGTCTGTTG

AATGTCGTGAAGGAAGCAGTTCCTCTGGAAGCTTCTTGAAGACAAACAA

CGTCTGTAGCGACCCTTTGCAGGCAGCGGAACCCCCCACCTGGCGACAG

GTGCCTCTGCGGCCAAAAGCCACGTGTATAAGATACACCTGCAAAGGCG

GCACAACCCCAGTGCCACGTTGTGAGTTGGATAGTTGTGAAAGAGTCA

AATGGCTCTCCTCAAGCGTATTCAACAAGGGGCTGAAGGATGCCCAGAA

GGTACCCCATTGTATGGGATCTGATCTGGGGCCTCGGTGCACATGCTTT

ACATGTGTTTAGTCGAGGTTAAAAAAACGTCTAGGCCCCCCGAACCACG

-continued
GGGACGTGGTTTTCCTTTGAAAAACACGATGATAATATGGCCACAACCA

TGGCGTCCGGATCTAGAATGGCTCTGCCCGTCACCGCTCTGCTGCTGCC

TCTGGCTCTGCTGCTGCACGCCGCACGCCCTGGGAGTCGCAAAGTCTGT

AATGGGATCGGCATCGGCGAGTTCAAGGACAGCCTGTCCATCAACGCCA

CCAATATCAAGCACTTTAAGAATTGCACATCTATCAGCGGCGACCTGCA

CATCCTGCCAGTGGCCTTCCGGGGCGATTCTTTTACCCACACACCCCCT

CTGGACCCTCAGGAGCTGGATATCCTGAAGACCGTGAAGGAGATCACAG

GCTTCCTGCTGATCCAGGCCTGGCCTGAGAACAGAACCGATCTGCACGC

CTTTGAGAATCTGGAGATCATCCGGGGCAGAACAAAGCAGCACGGCCAG

TTCTCCCTGGCCGTGGTGTCTCTGAACATCACCAGCCTGGGCCTGAGGT

CCCTGAAGGAGATCTCTGACGGCGATGTGATCATCTCCGGCAACAAGAA

CCTGTGCTACGCCAACACAATCAATTGGAAGAAGCTGTTTGGCACCTCT

GGCCAGAAGACAAAGATCATCTCTAACCGGGGCGAGAATAGCTGCAAGG

CAACCGGACAGGTGTGCCACGCACTGTGCAGCCCAGAGGGATGTTGGGG

CCCAGAGCCACGGGACTGCGTGAGCTGTAGAAACGTGTCCAGGGGCCGC

GAGTGCGTGGATAAGTGTAATCTGCTGGAGGGCGAGCCAAGGGAGTTCG

TGGAGAACTCCGAGTGCATCCAGTGTCACCCCGAGTGCCTGCCTCAGGC

CATGAACATCACCTGTACAGGCCGCGGCCCCGACAATTGCATCCAGTGT

GCCCACTATATCGATGGCCCTCACTGCGTGAAGACCTGTCCAGCCGGCG

TGATGGGCGAGAACAATACACTGGTGTGGAAGTACGCAGACGCAGGACA

CGTGTGCCACCTGTGCCACCCCAATTGCACCTATGGCTGTACAGGACCA

GGCCTGGAGGGATGCCCAACCAACGGCCCTAAGATCCCAAGCATCGCCA

CAGGCATGGTGGGGCACTGCTGCTGCTGCTGGTGGTGGCTCTGGGGAT

TGGGCTGTTTATGAGAAGGTAA

In embodiments of the present disclosure, a transgenic lymphocyte obtained by transducing the lentivirus into a lymphocyte has a targeted killing ability on tumor cells, especially on tumor cells highly expressing CD19, with moderate cell proliferation and decreased but safer production of cytokines. The obtained modified anti-CD19 CAR cells have safer anti-tumor activity.

In a fifth aspect, the present disclosure in embodiments provides a transgenic lymphocyte. According to embodiments of the present disclosure, the transgenic lymphocyte expresses a non-functional EGFR and an chimeric antigen receptor, wherein the chimeric antigen receptor comprises an extracellular segment, a trans-membrane segment and an intracellular segment, wherein the extracellular segment comprises a single-chain antibody region specifically binding to a tumor antigen and a hinge region, wherein the single-chain antibody region comprises a heavy chain variable region and a light chain variable region of the single-chain antibody and the tumor antigen is an antigen CD19, wherein the intracellular segment comprises an intracellular domain of immune co-stimulation molecule. The modified anti-CD19 CAR cells expressing the non-functional EGFR and the chimeric antigen receptor have a specific killing ability on tumor cells, especially on tumor cells highly expressing CD19, thus exhibiting safer anti-tumor activity.

In embodiments of the present disclosure, the transgenic lymphocyte as described above may further comprise at least one of the following additional technical features.

In embodiments of the present disclosure, the intracellular domain of the immune co-stimulation molecule is independently at least one selected from 4-1BB, OX-40, CD40L, CD27, CD30, CD28 and derivatives thereof. The expression of the intracellular domain of the immune co-stimulation molecule in embodiments can positively regulate and enhance the cellular immune response, thus improving the targeted killing ability of the transgenic lymphocytes on tumors. The co-expression of both the intracellular domain of the immune co-stimulation molecule and the non-functional EGFR ensures that the transgenic lymphocytes have a stronger targeted killing ability on tumors, with increased safety.

In embodiments of the present disclosure, the intracellular domain of immune co-stimulation molecule is an intracellular domain of 4-1BB. The intracellular domain of immune co-stimulation molecule of the chimeric antigen receptor in the transgenic lymphocyte of the present disclosure is the intracellular domain of 4-1BB. According to embodiments of the present disclosure, the intracellular domain of immune co-stimulation molecule is the intracellular domain of 4-1BB, thus enhancing the targeted killing ability of the transgenic lymphocyte.

In embodiments of the present disclosure, the non-functional EGFR expressed by the transgenic lymphocyte lacks the N-terminal ligand binding region and the activity of intracellular receptor tyrosine kinase, but includes the trans-membrane region of wild-type EGFR and the complete domain that binds to anti-EGFR antibody, thus the non-functional EGFR can be used as a suicide mark for the transgenic lymphocyte of the present disclosure. The co-expression of the non-functional EGFR and the chimeric antigen receptor can not only effectively ensure the targeted killing ability of the transgenic lymphocytes, but also allow the transgenic lymphocyte to be killed by anti-EGFR antibody when the patient has severe adverse reactions, thus further improving the safety of the transgenic lymphocytes on treating tumor patients with high CD19 expression.

In embodiments of the present disclosure, the transgenic lymphocyte is CD8+T lymphocyte. The transgenic lymphocyte as described above is capable of expressing both the non-functional EGFR and the antigen-specific chimeric antigen receptor, such as the CD19-specific chimeric antigen receptor, thus having targeted killing ability on tumors, with increased safety.

In embodiments of the present disclosure, the hinge region comprises an extracellular domain of human CD8 alpha (CD8α) of 55 amino acid residues and three alanine residues (AAA) located at the N-terminal of the extracellular domain of human CD8α; the trans-membrane segment comprises a trans-membrane domain of human CD8α linked to the hinge region of the extracellular segment; and the intracellular segment further comprises an intracellular domain of human CD8α, an intracellular domain of molecule 4-1BB and an intracellular domain of CD3 ζ chain, wherein the intracellular domain of human CD8α comprises seven amino acid residues and linked to the trans-membrane domain of human CD8α. The lymphocytes according to the present disclosure have strong tumor killing activity, with moderate cell proliferation and decreased production of cytokines, thereby reducing the side effects related to severe cytokine release syndrome and neurotoxicity.

In embodiments of the present disclosure, the transgenic lymphocyte is a natural killer (NK) cell or a natural killer T (NKT) cell.

In a sixth aspect, the present disclosure in embodiments provides a construct. According to embodiments of the present disclosure, the construct comprises a first nucleic acid sequence encoding the chimeric antigen receptor, and a second nucleic acid sequence encoding the non-functional EGFR, wherein the chimeric antigen receptor and the non-functional EGFR are as described above. According to embodiments of the present disclosure, the lymphocyte transduced with the construct successfully has a specific killing ability on tumor cells, especially has a targeted killing ability on tumor cells highly expressing CD19, with moderate cell proliferation and production of cytokines at a decreased but safer level, thus showing slow and lasting tumor killing properties. Therefore, the obtained modified anti-CD19 CAR-T cells have safer anti-tumor activity.

In embodiments of the present disclosure, the construct as described above may further comprise at least one of the following additional technical features.

In embodiments of the present disclosure, the first nucleic acid sequence and the second nucleic acid sequence are provided in the transgenic lymphocyte as described above to express the chimeric antigen receptor and the non-functional EGFR, wherein the chimeric antigen receptor and the non-functional EGFR are in a non-fused form. According to embodiments of the present disclosure, the first nucleic acid sequence and the second nucleic acid sequence are successfully provided in the transgenic lymphocyte, and the obtained transgenic lymphocyte can express both the non-functional EGFR and the chimeric antigen receptor (such as the CD19 specific chimeric antigen receptor) on cell membrane, wherein the chimeric antigen receptor and the non-functional EGFR are in a non-fused form. The lymphocytes according to the present disclosure have strong specific killing ability on tumors and higher safety.

In embodiments of the present disclosure, the construct further comprises: a first promoter operably linked to the first nucleic acid sequence, and a second promoter operably linked to the second nucleic acid sequence. According to embodiments of the present disclosure, the introduction of the first promoter and the second promoter allows the first nucleic acid sequence and the second nucleic acid sequence to be independently expressed, effectively ensuring the biological effect of the antigen targeting of the chimeric antigen receptor and the effective expression of the non-functional EGFR, thereby effectively ensuring the targeted killing ability of the lymphocytes on tumors, especially on tumor cells highly expressing CD19, thus ensuring the safety of immune killing.

In embodiments of the present disclosure, the first promoter and the second promoter are independently selected from CMV, EF-1, LTR and RSV promoters. According to embodiments of the present disclosure, the promoters as described above have the characteristics of high initiation efficiency and high specificity, thereby ensuring the efficient expression of the non-functional EGFR and the chimeric antigen receptor, thus further effectively ensuring the targeted killing ability and safety of the lymphocytes on tumors.

In embodiments of the present disclosure, the construct further comprises an internal ribosome entry site provided between the first nucleic acid sequence and the second nucleic acid sequence, wherein the internal ribosome entry site comprises the nucleotide sequence shown in SEQ ID NO: 13.

```
                                                    (SEQ ID NO: 13)
CCCCTCTCCCTCCCCCCCCCCTAACGTTACTGGCCGAAGCCGCTTGGAA

TAAGGCCGGTGTGCGTTTGTCTATATGTTATTTTCCACCATATTGCCGT

CTTTTGGCAATGTGAGGGCCCGGAAACCTGGCCCTGTCTTCTTGACGAG

CATTCCTAGGGGTCTTTCCCCTCTCGCCAAAGGAATGCAAGGTCTGTTG

AATGTCGTGAAGGAAGCAGTTCCTCTGGAAGCTTCTTGAAGACAAACAA

CGTCTGTAGCGACCCTTTGCAGGCAGCGGAACCCCCCACCTGGCGACAG

GTGCCTCTGCGGCCAAAAGCCACGTGTATAAGATACACCTGCAAAGGCG

GCACAACCCCAGTGCCACGTTGTGAGTTGGATAGTTGTGGAAAGAGTCA

AATGGCTCTCCTCAAGCGTATTCAACAAGGGGCTGAAGGATGCCCAGAA

GGTACCCCATTGTATGGGATCTGATCTGGGGCCTCGGTGCACATGCTTT

ACATGTGTTTAGTCGAGGTTAAAAAAACGTCTAGGCCCCCCGAACCACG

GGGACGTGGTTTTCCTTTGAAAAACACGATGATAATATGGCCACAACC
```

The introduction of the internal ribosome entry site allows the first nucleic acid molecule and the second nucleic acid molecule to be independently expressed. According to embodiments of the present disclosure, the introduction of the internal ribosome entry site ensures the biological effect of antigen targeting of the chimeric antigen receptor and the effective expression of the non-functional EGFR, resulting in a stronger targeted killing ability and increased safety of the lymphocytes on tumors.

In embodiments of the present disclosure, the construct further comprises a third nucleic acid sequence provided between the first nucleic acid sequence and the second nucleic acid sequence and encoding a linker peptide, wherein the linker peptide is cleavable in a lymphocyte. The introduction of the third nucleic acid sequence encoding the linker peptide allows the non-functional EGFR and the chimeric antigen receptor to be expressed on cell membrane in a non-fused form, which further ensures the biological effect of the non-functional EGFR and the chimeric antigen receptor. Therefore, the lymphocyte of the present disclosure has a stronger specific killing ability on tumors and increased safety.

In embodiments of the present disclosure, the linker peptide comprises the amino acid sequences shown in SEQ ID NOs: 14 to 17.

```
                                        (SEQ ID NO: 14)
(GSG) E G R G S L L T C G D V E E N P G P (SEQ ID NO: 15)
(GSG) A T N F S L L K Q A G D V E E N P G P (SEQ ID NO: 16)
(GSG) Q C T N Y A L L K L A G D V E S N P G P (SEQ ID NO: 17)
(GSG) V K Q T L N F D L L K L A G D V E S N P G P
```

The amino acid sequences shown in SEQ ID NOs: 14 to 17 are derived from the self-cleaving 2A peptides of foot-and-mouth disease virus F2A, equine rhinitis A virus E2A, porcine teschovirus P2A and thosea asigna virus T2A. The introduction of the linker peptide allows the non-functional EGFR and the chimeric antigen receptor to be expressed on cell membrane of the lymphocyte in a non-fused form. According to embodiments of the present disclosure, the introduction of the linker peptide ensures the biological effect of the non-functional EGFR and the chimeric antigen receptor, thus the lymphocytes of the present disclosure have stronger specific killing ability on tumors and increased safety.

In embodiments of the present disclosure, the vector of the construct is a non-pathogenic viral vector. The introduction of the non-pathogenic viral vector significantly improves the efficiency of replication and amplification of the construct in lymphocytes, thereby remarkably improving the efficient expression of the non-functional EGFR and the chimeric antigen receptors in lymphocytes, thus further enhances the targeting ability of the lymphocytes and improves the safety.

In embodiments of the present disclosure, the viral vector is at least one selected from retroviral vector, lentiviral vector and adenovirus-related viral vector. The viral vector of the present disclosure can perform widespread infection during the packaging and infection of viruses, including infection in both terminally differentiated cells and division-phase cells, with the genome integrated into or being free of the host chromosome, thereby achieving a broad-spectrum and efficient infection. Thus, the non-functional EGFR and the chimeric antigen receptor can be efficiently expressed in the lymphocytes, thus significantly improving the targeting ability of the lymphocytes on tumor cells especially the tumor cells highly expressing CD19, and increasing the safety.

In a seventh aspect, the present disclosure in embodiments provides a method for preparing the T lymphocyte or the transgenic lymphocyte as described above. According to embodiments of the present disclosure, the method comprises introducing the lentivirus or the construct as described above into a lymphocyte or a T lymphocyte. According to the method, the construct or the lentivirus is successfully introduced into the lymphocyte or the T lymphocyte as described above, achieving the expression of the non-functional EGFR and the chimeric antigen receptor in the lymphocytes, indicating that the T lymphocyte or the transgenic lymphocyte prepared by the method has a targeted killing ability on tumor cells, especially on tumor cells highly expressing CD19, with moderate cell proliferation and production of cytokines at a decreased but safer level, thus showing slow and lasting tumor killing properties. Therefore, the obtained modified anti-CD19 CAR-T cells have safer anti-tumor activity.

In an eighth aspect, the present disclosure in embodiments provides a therapeutic composition for treating a cancer. According to embodiments of the present disclosure, the therapeutic composition comprises the anti-CD19 chimeric antigen receptor, the construct, the lentivirus and the T lymphocyte or the transgenic lymphocyte as described above. Any component of the therapeutic composition as described above can achieve efficient expression of the non-functional EGFR and the chimeric antigen receptor in the transgenic lymphocyte or the T lymphocyte, thus the obtained transgenic lymphocyte or T lymphocyte can have the targeted killing ability on tumors. Therefore, the therapeutic composition for treating a cancer of present disclosure has the targeted killing ability on tumor cells especially on tumor cells highly expressing CD19 and has increased safety.

In embodiments of present disclosure, the therapeutic composition as described above may further comprise at least one of the following additional technical features.

In embodiments of present disclosure, the tumor cells of the cancer highly express CD19. The therapeutic composition of present disclosure can achieve efficient expression of the non-functional EGFR and the chimeric antigen receptor (such as the anti-CD19 chimeric antigen receptor) in cell membrane of the transgenic lymphocyte or T lymphocyte which has a targeted killing on tumor cells highly expressing CD19, with increased safety.

In a ninth aspect, the present disclosure in embodiments provides a method for improving safety of lymphocyte therapy, comprising allowing the lymphocyte to express the chimeric antigen receptor and the non-functional EGFR. The chimeric antigen receptor, the non-functional EGFR and the lymphocyte are as described above. The non-functional EGFR lacks the N-terminal ligand binding region and the activity of intracellular receptor tyrosine kinase, but includes the trans-membrane region of wild-type EGFR and the complete amino acid sequence that binds to anti-EGFR antibody, thus the non-functional EGFR can be used as a suicide mark for lymphocytes. Therefore, when applied in the treatment of tumor cells highly expressing CD19, the T lymphocytes of the present disclosure are capable of proliferating moderately and releasing cytokines at a decreased but safer level. Further, the lymphocytes of the present disclosure can be killed by anti-EGFR antibody when the patient has severe adverse reactions, thus exhibiting tumor killing property with increased safety.

In a tenth aspect, the present disclosure in embodiments provides a method for treating a cancer, comprising administering the construct, the lentivirus, the T lymphocyte, the transgenic lymphocyte or the anti-CD19 chimeric antigen receptor as described above to a patient in need. When the method for treating a cancer of the present disclosure is applied in treating a cancer (i.e., killing tumor cells), the T lymphocytes are capable of proliferating moderately and releasing cytokines at a decreased but safer level. Further, the lymphocyte can be killed by anti-EGFR antibody when the patient has severe adverse reactions. Therefore, the method for treating a cancer of the present disclosure has a safer tumor treatment effect.

In embodiments of present disclosure, the method for treating a cancer may further comprise at least one of the following additional technical features.

In embodiments of present disclosure, the tumor cells of the cancer highly express CD19. The method for treating a cancer according to the present disclosure has a strong killing ability on tumor cells highly expressing CD19.

In embodiments of present disclosure, the cancer comprises leukemia or lymphoma. The method for treating a cancer according to the present disclosure has a strong treatment effect on treating leukemia or lymphoma, with increased safety.

DETAILED DESCRIPTION

Reference will be made in detail to examples of the present disclosure. The examples described herein with reference are explanatory, illustrative, and used to generally understand the present disclosure. The examples shall not be construed to limit the present disclosure.

According to the examples of present disclosure, the term of "anti-CD19 CAR" refers to an anti-CD19 chimeric antigen receptor, the term of "anti-CD19 CAR cell" refers to a cell expressing anti-CD19 CAR, and the term of "anti-CD19 CAR-T cell" refers to a T cell expressing anti-CD19 CAR, unless otherwise specified.

Chimeric Antigen Receptor

In one aspect, the present disclosure provides a chimeric antigen receptor.

According to embodiments of the present disclosure, the chimeric antigen receptor comprises:

an extracellular segment, comprising a single-chain antibody region specifically binding to an antigen human CD19 and a hinge region, wherein the single-chain antibody region comprises a heavy chain variable region and a light chain variable region of the single-chain antibody, and the hinge region comprises an extracellular domain of human CD8 alpha (CD8α) of 55 amino acid residues and three alanine residues (AAA) located at the N-terminal of the extracellular domain of human CD8α, a trans-membrane segment, comprising a trans-membrane domain of human CD8α linked to the hinge region of the extracellular segment and embedded in cell membrane of T lymphocyte, and an intracellular segment, comprising an intracellular domain of human CD8α, an intracellular domain of molecule 4-1BB and an intracellular domain of CD3 ζ chain, wherein the intracellular domain of human CD8α comprises seven amino acid residues and linked to the trans-membrane domain of human CD8α.

Compared to the prior art, the modified chimeric antigen receptor according to embodiments of the present disclosure has improved spatial configuration, thus the T lymphocytes expressing the modified chimeric antigen receptor have strong tumor killing ability while having reduced cell proliferation and decreased production of cytokines. Thus, when the lymphocytes expressing the modified chimeric antigen receptor are applied in treating tumor patients, the side effects related to severe cytokine release syndrome and neurotoxicity are reduced.

Figure 1:
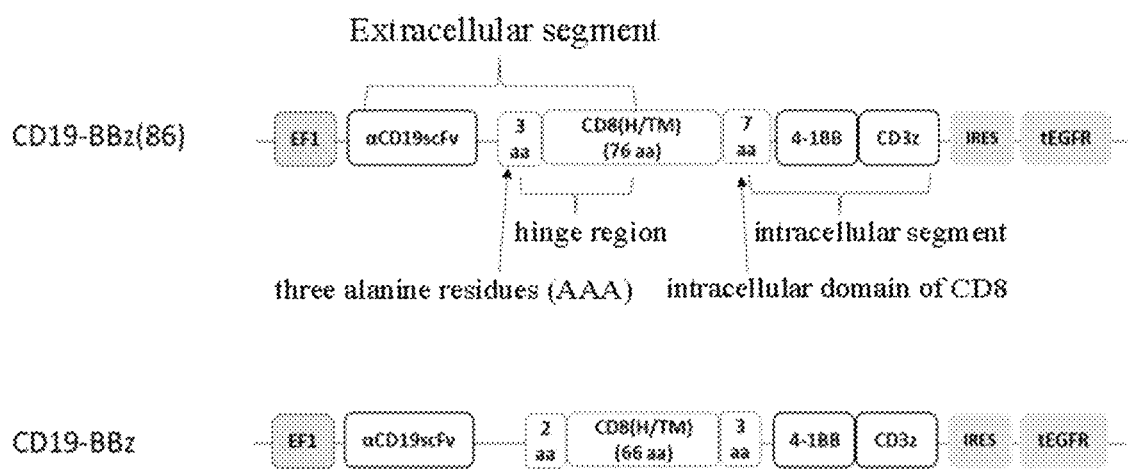
FIG. 1 shows a schematic diagram of a lentiviral vector containing anti-CD19 CAR according to embodiments of the present disclosure.

In comparison with the prior art, the hinge region of the chimeric antigen receptor of the present disclosure comprises the extracellular domain of human CD8 alpha (CD8α) (consisting of the 55 amino acid residues) and three alanine residues (AAA), and has the amino acid sequence shown in SEQ ID NO: 7 (FIG. 1). The trans-membrane segment of the chimeric antigen receptor of the present disclosure comprises the trans-membrane domain of human CD8α consisting of the 21 amino acid residues, and has the amino acid sequence shown in SEQ ID NO: 5 (FIG. 1). The intracellular segment of the chimeric antigen receptor of the present disclosure comprises the intracellular domain of human CD8α consisting of the 7 amino acid residues, and has the amino acid sequence shown in SEQ ID NO: 3 (FIG. 1). The amino acid sequences of the hinge region, the trans-membrane segment and the intracellular segment of the chimeric antigen receptor in the present disclosure are different from those of the chimeric antigen receptor of the prior art, thus the modified anti-CD19 CAR of the present disclosure has a spatial configuration different from that of the anti-CD19 CAR of the prior art. The present inventors surprisingly discovered that the T lymphocytes expressing the modified chimeric antigen receptor have strong tumor killing activity while having reduced cell proliferation and decreased production of cytokines, resulting in a moderate but safer tumor killing activity.

T Lymphocyte or Transgenic Lymphocyte

In another aspect, the present disclosure provides a T lymphocyte or a transgenic lymphocyte. According to embodiments of the present disclosure, the T lymphocyte expresses a non-functional epidermal growth factor receptor (EGFR) and the anti-CD19 chimeric antigen receptor as defined above. The non-functional EGFR lacks the N-terminal ligand binding region and the activity of intracellular receptor tyrosine kinase, but includes the trans-membrane region of wild-type EGFR and the complete amino acid sequence that binds to anti-EGFR antibody, thus the non-functional EGFR can be used as a suicide mark for lymphocytes. The T lymphocyte or transgenic lymphocyte express the anti-CD19 chimeric antigen receptor and has a targeted killing ability on tumor cells, especially on tumor cells highly expressing CD19, with moderate cell proliferation and decreased production of cytokines, showing a slow and lasting tumor killing properties. The obtained modified anti-CD19 CAR-T cells have a safer anti-tumor activity.

In addition, according to embodiments of the present disclosure, the non-functional EGFR lacks the N-terminal ligand binding region and the activity of intracellular receptor tyrosine kinase, but includes the trans-membrane region of wild-type EGFR and the complete amino acid sequence that binds to anti-EGFR antibody, thus the non-functional EGFR can be used as a suicide mark for lymphocytes. The lymphocytes expressing the non-functional EGFR can be killed by the anti-EFGR antibodies in vivo. Therefore, the T lymphocytes or transgenic lymphocytes expressing the non-functional EGFR can not only ensure the targeted killing ability, but also be killed by the anti-EGFR antibody when the patient has severe adverse reactions, thus improving the safety on treatment of tumor patients with high CD19 expression.

In addition, according to embodiments of the present disclosure, the antibody in the extracellular segment of the chimeric antigen receptor as described above is a single-chain antibody. The present inventors discovered that the single-chain antibody can remove the competitive surface proteins in non-specific reaction, and the single-chain antibody is more easily penetrated into tumor tissues so as to increase the therapeutic concentration of drugs.

The transgenic lymphocytes according to the embodiment of the present disclosure express the chimeric antigen receptor containing the single-chain antibody, thus further improving the targeted killing ability on tumor cells.

According to another embodiment of the present disclosure, the antigen bound by the single-chain antibody as described above is CD19. Therefore, the transgenic lymphocytes of the present disclosure have a targeted killing ability on cells expressing the antigen CD19, with stronger specific binding between the antigen and the single-chain antibody. Thus, the transgenic lymphocytes of the present disclosure have enhanced targeted killing on tumor cells expressing the antigen CD19.

In addition, according to embodiments of the present disclosure, the intracellular domain of the immune co-stimulation molecule is independently at least one selected from 4-1BB, OX-40, CD40L, CD27, CD30, CD28 and derivatives thereof. The expression of the intracellular domain of the immune co-stimulation molecule can positively regulate and enhance the cellular immune response, thus improving the targeted killing ability of the transgenic lymphocytes on tumor cells highly expressing CD19. The co-expression of both the intracellular domain of the immune co-stimulation molecule and the non-functional EGFR ensures that the transgenic lymphocytes have a more effective and safer immune-killing ability.

According to embodiments of the present disclosure, the transgenic lymphocyte is a cytotoxic T lymphocyte, a natural killer (NK) cell or a natural killer T (NKT) cell. The cytotoxic T cells are also called killer T cells. The natural killer cells are a type of immune cells that non-specifically recognize target cells. The natural killer T cells are a subset of T cells that comprise receptors of the T cell and the natural killer cell. The transgenic lymphocytes as described above co-express the non-functional EGFR and the chimeric antigen receptor, thus having a more effective and safer immune-killing ability.

Lentivirus or Construct

In another aspect, the present disclosure provides a lentivirus or a construct. According to embodiments of the present disclosure, the lentivirus or the construct carries a first nucleic acid molecule encoding a chimeric antigen receptor, wherein the chimeric antigen receptor comprises the amino acid sequence shown in SEQ ID NO: 8 and the first nucleic acid molecule comprises the nucleotide sequence shown in SEQ ID NO: 9, and a second nucleic acid molecule encoding a non-functional EGFR, wherein the non-functional EGFR comprises the amino acid sequence shown in SEQ ID NO: 10 and the second nucleic acid molecule comprises the nucleotide sequence shown in SEQ ID NO: 11. According to embodiments of the present disclosure, the transgenic lymphocyte obtained by transducing the lentivirus or construct into a lymphocyte can express both the non-functional EGFR and the anti-CD19 chimeric antigen receptor on cell membrane, thus having strong targeted killing ability on tumor cells, with moderate cell proliferation and decreased production of cytokines, thus showing slow and lasting tumor killing properties. Therefore, the obtained modified anti-CD19 CAR-T cells have safer anti-tumor activity.

According to embodiments of the present disclosure, the lentivirus or construct comprises the nucleotide sequence shown in SEQ ID NO: 12. The nucleotide sequence shown in SEQ ID NO: 12 encodes both the non-functional EGFR and the anti-CD19 chimeric antigen receptor (CD19 CAR/tEGFR). According to an embodiment of the present disclosure, the transgenic lymphocyte obtained by transducing the lentivirus described in this embodiment into a lymphocyte can express both the non-functional EGFR and the anti-CD19 chimeric antigen receptor, thus having strong targeted killing ability on tumor cells highly expressing CD19, with moderate cell proliferation and decreased production of cytokines, thus showing slow and lasting tumor killing properties. Therefore, the obtained modified anti-CD19 CAR-T cells have safer anti-tumor activity.

According to embodiments of the present disclosure, the independent expression of the non-functional EGFR and the anti-CD19 chimeric antigen receptor as described above is achieved by at least one of the following methods.

Internal ribosome entry site (IRES): An internal ribosome entry site is provided between the first nucleic acid sequence encoding the chimeric antigen receptor and the second nucleic acid sequence encoding the non-functional EGFR, wherein the internal ribosome entry site comprises the nucleotide sequence shown in SEQ ID NO: 13. The internal ribosome entry site is usually located in the 5' untranslated region (UTR) of the RNA virus genome, such that the translation of one protein can be independent of the 5' cap structure, while the translation of another protein is dependent on the 5' cap structure, thus allowing the proportional expression of two genes before and after the IRES. The introduction of the internal ribosome entry site allows the independent expression of the first nucleic acid sequence encoding the chimeric antigen receptor and the second nucleic acid sequence encoding the non-functional EGFR. According to embodiments of the present disclosure, the introduction of the internal ribosome entry site effectively ensures the efficient expression of the chimeric antigen receptor and the non-functional EGFR, which further improves the specific killing of the lymphocytes on tumor cells, with increased safety.

Third nucleic acid sequence: A third nucleic acid sequence is provided between the first nucleic acid sequence and the second nucleic acid sequence and encoding a linker peptide, wherein the linker peptide is cleavable in a lymphocyte. According to embodiments of the present disclosure, the linker peptide comprises the amino acid sequences shown in SEQ ID NOs: 14 to 17. The introduction of the third nucleic acid sequence allows the non-functional EGFR and the chimeric antigen receptor to be expressed on cell membrane of the lymphocyte in a non-fused form, thus ensuring the biological effect of the non-functional EGFR and the chimeric antigen receptor and further ensuring a stronger specific killing of the lymphocytes on tumor cells, with increased safety.

Promoter: A first promoter is operably linked to the first nucleic acid sequence encoding the chimeric antigen receptor, and a second promoter is operably linked to the second nucleic acid sequence encoding the non-functional EGFR. According to embodiments of the present disclosure, the first promoter and the second promoter are independently selected from CMV, EF-1, LTR and RSV promoters. The introduction of the first promoter and the second promoter allows the independent expression of the first nucleic acid sequence encoding the chimeric antigen receptor and the second nucleic acid sequence encoding the non-functional EGFR, thereby ensuring the efficient expression of the chimeric antigen receptor, thus further improving the targeting ability and specific killing ability of the lymphocytes on tumor cells with increased safety.

The introduction of the internal ribosome entry site or the first promoter and the second promoter allows efficient expression of the non-functional EGFR and the chimeric antigen receptor on cell membrane of the transgenic lymphocyte of the present disclosure, thereby ensuring the biological effect of the chimeric antigen receptor, effectively killing the undesired transgenic lymphocytes timely, thus further improving the targeting ability and specific killing ability of the lymphocytes on tumor cells with increased safety.

In addition, according to embodiments of the present disclosure, the vector of the construct is a non-pathogenic viral vector. The introduction of the non-pathogenic viral vector significantly improves the efficiency of replication and amplification of the construct in the lymphocytes, which further improves the targeting ability and specific killing ability of the lymphocytes on tumor cells with increased safety.

According to embodiments of the present disclosure, the vector of the construct is a viral vector, which is at least one selected from retroviral vector, lentiviral vector, adenovirus vector and adenovirus-related viral vector. According to embodiments of the present disclosure, the viral vector can perform widespread infection during the packaging and infection of viruses, including infection in both terminally differentiated cells and division-phase cells, with the genome integrated into or being free of the host chromosome, thereby achieving a broad-spectrum and efficient infection, thus the non-functional EGFR and the chimeric antigen receptor can be efficiently expressed in the lymphocytes, allowing significantly improved targeting ability and specific killing ability of the lymphocytes on tumor cells, with increased safety.

According to a specific embodiment of the present disclosure, taking the construction of a lentiviral vector as an example, the inventors inserted the target nucleic acid sequence into the viral genome at a position to construct a replication-deficient lentiviral vector. Then, the inventors have constructed a packaging cell line containing gag, pol and env genes but without LTR and packaging sequence for obtaining the lentivirus. The recombinant lentiviral transgenic plasmid containing the target nucleic acid sequence, along with the LTR and packaging sequence of lentivirus are introduced into the packaging cell line, in which the packaging sequence allows the transcript of the recombinant lentiviral transgenic plasmid to be packaged into the lentivirus and then secreted into the culture medium. Subsequently, the culture medium containing the recombinant lentivirus is collected by the inventors, followed by selectively concentrating and transferring genes. The lentivirus vector can infect a variety of cell types, including divisible and non-divisible cells.

In addition, according to embodiments of the present disclosure, the lentivirus is a recombinant lentivirus, which contains not only common lentiviral genes (gag, pol and env) but also other genes with regulatory and structural functions. The lentivirus vectors are well known to those skilled in the art and comprise human immunodeficiency virus (HIV-1, HIV-2) and simian immunodeficiency virus (SIV). The lentivirus vectors are produced by multiply attenuating HIV pathogenic genes, such as deleting all of genes (i.e., genes env, vif, vpr, vpu and nef), thus obtaining lentiviral vectors as a bio-safe vector. The recombinant lentivirus can infect non-dividing cells and can be used for transferring genes and expressing the nucleic acid sequence in vivo and in vitro. For example, in an appropriate host cell, two or more lentivirus vectors with packaging sequences (gag, pol, env, rev, and tat) can infect non-dividing cells. The targeting ability of the recombinant virus is achieved through the binding of the antibody or specific ligand targeting specific cell receptor to the membrane protein. Meanwhile, the specific targeting ability of the recombinant virus can be obtained by inserting an effective sequence including the regulatory region, along with another sequence encoding the ligand that binds to the receptor of a specific target cell, into the viral vector. Various effective lentiviral vectors, as well as vectors produced by various methods and operations, are useful in regulating cell expression.

According to embodiments of the present disclosure, the adenovirus-related viral vector (AAV) can be constructed by using DNA of one or more well-known serotype adenovirus-related virus vectors. Those skilled in the art are able to construct an appropriate adenovirus-related viral vector to carry nucleotide sequence that co-expresses the chimeric antigen receptor and the non-functional EGFR.

In addition, micro-genes are included according to embodiments of the present disclosure, indicating that sequence combination including the selected nucleotide sequence and necessarily and operably linking sequence is used to direct transformation, transcription and/or expression of gene products in vivo or in vitro in host cells. The "operably linking sequence" comprises the expression control sequence of continuous target genes and the expression control sequence for trans- or remote controlling target genes.

In addition, the vectors in embodiments of the present disclosure further comprise conventional control components, which allows the transcription or expression of transformed mRNA along with plasmid vectors during cell transfection or/and along with viral vectors during cell infection. A large number of expression control sequences (including natural, inducible and/or tissue-specific promoters) may be used. According to an embodiment of the present disclosure, the promoter is a RAN polymerase promoter selected from pol I, pol II and pol III. According to an embodiment of the present disclosure, the promoter is a tissue-specific promoter. According to an embodiment of the present disclosure, the promoter is an inducible promoter. According to an embodiment of the present disclosure, the promoter is selected from a promoter based on the selected vector. According to an embodiment of the present disclosure, the promoter is CMV IE gene, EF-1α, ubiquitin C or phosphoglycerol kinase (PGK) promoter for selection of lentiviral vector. Other conventional expression control sequences include selectable markers or reporter genes, including nucleotide sequences encoding geneticin, hygromycin, ampicillin or puromycin resistance proteins. Other components of the vectors include the origin of replication.

The techniques for constructing vectors are well known to those skilled in the art, which includes conventional cloning techniques, such as polymerase chain reaction used in the present disclosure and any appropriate method for providing required nucleotide sequence.

According to embodiments of the present disclosure, the inventors have constructed a viral vector co-expressing the non-functional EGFR and the chimeric antigen receptor (CAR). The viral vector or plasmid expressing the non-functional EGFR and the chimeric antigen receptor (CAR) may be complex, which can be combined with polymers or other materials to improve its stability, or assist its targeting movement Method for Preparing the Transgenic Lymphocyte In another aspect of the present disclosure, the present disclosure provides a method for preparing the T lymphocyte or the transgenic lymphocyte as described above. According to embodiments of the present disclosure, the method comprises introducing the construct or the lentivirus as described above into a lymphocyte or a T lymphocyte. The introduction can be performed by electroporation or virus infection of host cells. According to the embodiment, the construct or the lentivirus is introduced into a lymphocyte or a T lymphocyte successfully which allows the expression of the non-functional EGFR and the anti-CD19 chimeric antigen receptor, such that the transgenic lymphocyte or transgenic T lymphocyte introduced with the construct or lentivirus has a specific killing ability on tumor cells, especially on tumor cells that highly express CD19, with moderate cell proliferation and decreased production of cytokines and showing a slow and lasting tumor killing properties. The obtained modified anti-CD19 CAR-T cells have safer anti-tumor activity.

Therapeutic Composition for Treating a Cancer

In a further aspect of the present disclosure, the present invention provides a therapeutic composition for treating a cancer. According to embodiments of the present disclosure, the therapeutic composition comprises: the anti-CD19 chimeric antigen receptor, the construct, the lentivirus, the T lymphocyte or the transgenic lymphocyte as described above. Any component of the therapeutic composition as described above can achieve efficient expression of the non-functional EGFR and the anti-CD19 chimeric antigen receptors in the transgenic lymphocyte or the T lymphocyte, thus the obtained transgenic lymphocyte or T lymphocyte can have the targeted killing ability on tumor cells that highly express CD19, with moderate cell proliferation, decreased production of cytokines and safer immune killing.

According to embodiments of the present disclosure, when administered to patients, the therapeutic composition is appropriately prepared in a biocompatible solution or a pharmaceutically acceptable carrier. The various therapeutic compositions prepared are suspended or dissolved in pharmaceutically or physiologically acceptable carriers, such as saline, isotonic saline solution or other obvious formulas of skilled in the art. The appropriate carrier largely depends on the route of administration. Other aqueous or anhydrous isotonic sterile injections and suspensions are pharmaceutically acceptable carriers.

According to embodiments of the present disclosure, a sufficient number of viral vectors are transduced into T cells, thus a sufficient amount of the target gene (i.e., transgene) is provided to express the non-functional EGFR and the anti-CD19 chimeric antigen receptor. The dosage of the therapeutic composition mainly depends on the condition, age, weight and health of the patient to be treated, which may cause difference between patients.

These methods expressing the non-functional EGFR and the anti-CD19 chimeric antigen receptor are a part of the combination therapy. These viral vectors and anti-tumor T cells used in adoptive immunotherapy can be performed alone or in combination with other cancer treatment methods. A treatment method can utilize one or more drug therapies under suitable conditions.

According to embodiments of the present disclosure, the tumor cells of the cancer highly express CD19. The transgenic lymphocyte or T lymphocyte highly express the non-functional EGFR and the chimeric antigen receptor, thus has a targeted killing ability on tumor cells, especially on tumor cells that highly express CD19, with safer and effective immune killing.

Method for Improving Safety of Lymphocyte Therapy

In a further aspect, the present disclosure provides a method for improving safety of lymphocyte therapy, which comprises allowing the lymphocyte to express the chimeric antigen receptor and the non-functional EGFR. The non-functional EGFR, the lymphocyte and the chimeric antigen receptor are as described above. The non-functional EGFR lacks the N-terminal ligand binding region and the activity of intracellular receptor tyrosine kinase, but includes the trans-membrane region of wild-type EGFR and the complete amino acid sequence that binds to anti-EGFR antibody, thus the non-functional EGFR can be used as a suicide mark for lymphocytes. Therefore, when applied in treating tumor cells highly expressing CD19, the T lymphocyte of the present disclosure exhibits moderate cell proliferation, decreased but safer production of cytokines, and further can be killed by anti-EGFR antibody when the patient has severe adverse reactions, thereby reducing the side effects related to severe cytokine release syndrome and neurotoxicity, with safer and effective immune killing.

The present disclosure is further descried with reference to the following examples.

It would be appreciated by those skilled in the art that the following examples are explanatory and cannot be construed to limit the scope of the present disclosure. If the specific technology or conditions are not specified in the examples, a step will be performed in accordance with the techniques or conditions described in the literature in the art (for example the "Molecular Cloning Experiment Guide" J. Sambrook et al., translated by Huang Peitang et al., the third edition, Science Press), or in accordance with the product instructions. If the manufacturers of reagents or instruments are not specified, the reagents or instruments may be commercially available.

Example 1

The cell lines and basic experimental techniques used in examples of the present disclosure are described as follows.
Production of Lentivirus and Transduction of Human T Lymphocyte A replication-deficient lentiviral vector was produced and then collected by centrifugation for subsequent transduction of human T lymphocyte. The experimental process of production and collection of lentiviral vectors were briefly described. 293T cells were plated in a cell-culture dish with a bottom area of 150 cm$^2$ followed by lentivirus transduction by using Express-In (purchased from OPEN Biosystems/THERMO SCIENTIFIC, Waltham, Mass.) according to the instructions, in which 15 μg of lentiviral transgenic plasmids, 5 μg of VSV glycoprotein expression plasmids (pVSV-G), 10 μg of pCMVR8.74 plasmids (Gag/Pol/Tat/Rev expression plasmids) and 174 μl of Express-In with a concentration of 1 μg/μl were added into each cell-culture dish containing the 293T cells. After that, the supernatant at 24 hours and 48 hours was collected respectively, followed by centrifuged at 28,000 rpm for 2 hours by using an ultracentrifuge with a centrifuge rotor (Beckman SW 32 Ti, purchased from BECKMAN COULTER, Brea, Calif.). The lentiviral plasmid pellets were resuspended with 0.75 ml of Roswell Park Memorial Institute (RPMI)-1640 medium.

Primary human T lymphocytes isolated from healthy donors were cultured in the RPMI-1640 medium and activated by magnetic beads coated with monoclonal antibodies against CD3 and CD28 (purchased from INVITROGEN, Carlsbad, Calif.). The human T lymphocytes were transduced using spin-implantation at 18 to 24 hours after the activation. Specifically, 0.5×10$^6$ T lymphocytes were plated in each well of a 24-well plate and the 0.75 ml of resuspended lentiviral plasmid liquid and Polybrene (with a concentration of 8 μg/ml) were added to the each well. The mixture of T lymphocytes and lentiviral plasmids was centrifuged in a benchtop centrifuge (purchased from SORVALL ST 40, THERMO SCIENTIFIC) at 2,500 rpm and room temperature for 90 minutes. Human recombinant interleukin-2 IL-2 (purchased from NOVARTIS, Basel, Switzerland) in a final concentration of 100 IU/ml was added into the RPMI-1640 medium containing T lymphocytes every 2 to 3 days and the cell density of T lymphocytes was kept at 0.5×10$^6$ to 1×10$^6$ cells/mL during culturing of T lymphocytes. Once falling dormant such as occurring slower cell growth and decreased cell size or at a certain planned point time, the transduced T lymphocytes were subjected to functional analysis. The cell growth and cell size were evaluated by Coulter Counter (purchased from Beckman Coulter).

The flow cytometer BD FACSCanto II (purchased from BD BIOSCIENCES) was used in the examples of the present disclosure and the flow cytometry data was analyzed using FlowJo version 7.2.5 software (purchased from TREE STAR, Ashland, Oreg.).
Antibody Dependent Cell Mediated Cytotoxicity (ADCC)

In the example related to ADCC, lymphocytes expressing non-functional EGFR were detected with the 4-hour-$^{51}$Cr-release method on evaluation of the cell-dependent lysis ability induced by anti-EGFR antibody. The human T lymphocytes transduced with the lentiviral vectors were used as target cells. 100 μl Ci Na$_2^{51}$CrO$_4$ (purchased from GE HEALTHCARE LIFE SCIENCES, Marlborough, Mass.) was used to label 2-5×10$^6$ target cells by incubation at 37° C. for 1 hour with shaking. The labeled target cells were washed three times with phosphate buffer saline (PBS) and resuspended with medium to a cell density of 1×10$^5$ cells/ml. Then, 50 μl of the medium containing 5×10$^3$ labeled cells were added to each well of a 96-well plate for cell plating and 50 μl of anti-EGFR antibody (purchased from ERBITUX, Genentech) was added to a final concentration of 20 μg/ml, was and then incubated at room temperature for 30 minutes. Meanwhile, another medium containing 5×10$^3$ labeled cells in each well was added with 50 μl of a normal medium without anti-EGFR antibody so as to detect the spontaneous release of $^{51}$Cr. Besides, Triton X-100 with a final concentration of 1% was added to ensure the maximum release of $^{51}$Cr. In the following examples related to ADCC, human peripheral blood mononuclear cells (PBMC, effector cells) with 5×10$^5$ cells/well were added to the 96-well plate, followed by incubating at 37° C. overnight. On the next day, the supernatant was collected to determine the release of $^{51}$Cr via count per minute (cpm) value calculated with a gamma (γ) counter. The cytotoxicity ratio was calculated with the following formula: % specific lysis=(experimental release cpm value−spontaneous release cpm value)/(maximum release cpm value−spontaneous release cpm value)× 100, where the maximum release cpm value was obtained by the additional addition of Triton X-100 to the target cells and the spontaneous release cpm value was obtained in the absence of both anti-EGFR antibody and effector cell.
$^{51}$Cr Release Experiment In the example, the 4-hour-$^{51}$Cr-release method was applied to evaluate the cytotoxic activity of the anti-CD19 chimeric antigen receptor T cells (i.e., anti-CD19 CAR-T lymphocytes), which includes the following specific steps. Target test cells were labeled with $^{51}$Cr at 37° C. for 1 hour, followed by washing the labeled test cells with RPMI medium containing 10% fetal calf serum (FCS). The washed cells were resuspended in the RPMI medium containing 10% FCS to a concentration of 1×10$^5$ cells/ml. The transduced T cells were added into the suspension of the target test cells at different ratios of effector cells and target cells (E:T) and then inoculated to a 96-well plate with a volume of 200 μl per well. The cells were cultured in an incubator at 37° C. for 4 hours. After that, 30 μl of supernatant in each well was placed in a 96-micro well plate of a counter (i.e., a top counting NXT micro scintillation counter, purchased from PACKARD BIOSCIENCE) for counting analysis. The number of effector cells in each counting well was determined based on the total number of transduced T cells. The labeled target test cells were human pleural mesothelioma cells from ATCC, CD19$^+$ MSTO-211H cells.

Example 2 Construction of a Vector Co-Expressing Non-Functional EGFR and Anti-CD19 Chimeric Antigen Receptor In this example, the present inventors artificially synthesized a sequence encoding the anti-human CD19 single-chain antibody, human CD8α, intracellular domain of molecule 4-1BB and CD3 ζ chain of T cell receptor, as well as XbaI and BstBI cloning sites at both ends. The artificially synthesized sequence was cloned into a shuttle plasmid of lentiviral vector containing EF-1 promoter (i.e., PCDH-EF1-MCS-IRES-GFP, SYSTEM BIOSCIENCES, Palo Alto, Calif.) by XbaI and BstBI double enzyme digestion, ligation, screening and amplification in target plasmid. Further, the inventors artificially synthesized a sequence encoding non-functional tEGFR and BspEI and SalI cloning sites at both ends, and then constructed a shuttle plasmid of lentiviral vector co-expressing non-functional tEGFR and anti-CD19 chimeric antigen receptor (named as LV-CD19-BBz (86)) by double enzyme digestion, ligation, screening and amplification in target plasmid.

FIG. 1 shows a schematic diagram of the LV-CD19-BBz (86) lentiviral vector, which contains the sequence encoding the modified anti-CD19 chimeric antigen receptor, IRES and non-functional tEGFR. The anti-CD19 chimeric antigen receptor was expressed under the regulation of the EF-1 promoter, and the non-functional tEGFR as a separate mRNA transcription unit was translated after the sequence of IRES. The method of constructing the lentiviral vector LV-CD19-BBz expressing CD19-BBz (CTL019) (Kymriah) in the prior art is described in Imai, C. et al. Leukemia. 2004; 18: 676-684; Milone M C, et al. Mol her. 2009; 17: 1453-64.

Figure 2:
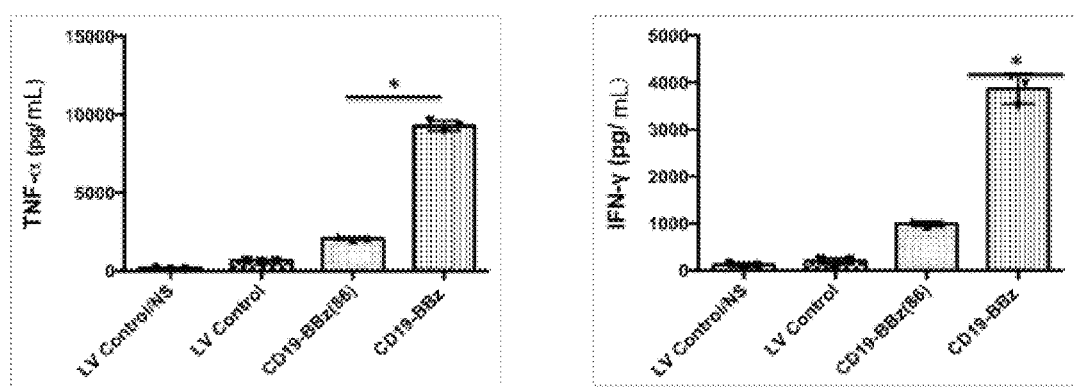
FIG. 2 is a graph showing the production of cytokines under co-culture of anti-CD19 CAR-T cells transduced with various recombinant lentiviral vectors and CD19+ tumor cells according to embodiments of the present disclosure.
Figure 2:
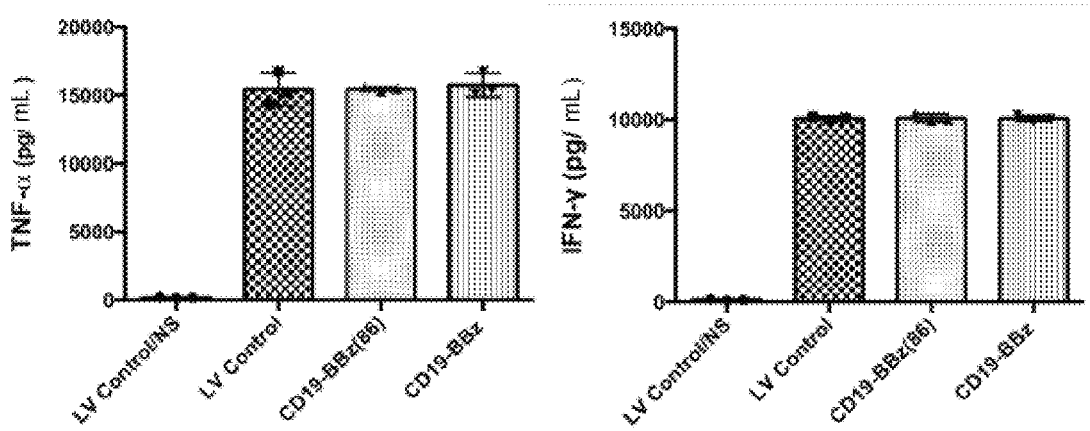

Example 3 Significantly Reduced Secretion of Cytokines by the Improved LV-CD9-BBz (86) CAR-T Lymphocyte In this example, peripheral blood lymphocytes taken from anonymous donors were separated by gradient centrifugation using the gradient centrifuge Ficoll-Hypaque. The T lymphocytes and T lymphocyte activating magnetic beads coated with monoclonal antibodies against CD3/CD28 (purchased from INVITROGEN, Carlsbad, Calif.) were incubated in the advanced RPMI medium 1640 with 2 mmol/L glutamine, 10% high-temperature inactivated fetal calf serum (FCS) (purchased from SIGMA-ALDRICH Co.) and 100 U/ml penicillin/streptomycin (purchased from INVITROGEN GIBCO, Cat. no. 12633-012) at 5% $CO_2$ and 37° C. for 72 hours. After activation and culturing for 72 hours, the T cells were washed with the washing buffer to remove the magnetic beads. The washed T cells were inoculated to cell culture dishes coated with recombinant fibronectin fragments (FN ch-296, RETRONECTIN). After that, the T cells were transduced with lentiviruses of the improved LV-CD19-BBz (86), LV-CD19-BBz of the prior art, or blank vector LV-control expressing tEGFR only, which was conducted as described in Example 1. The transduced T cells were cultured in the RPMI-1640 medium and induced with recombinant human IL-2 factor (100 ng/ml, purchased from R&D SYSTEMS) for 7-10 days for amplification, and then co-cultured with irradiated CD19-positive Raji tumor cells. The inventors measured the concentration of various cytokines in the co-cultured supernatant using ELISA method. The results in FIG. 2A showed that the concentration of various cytokines produced by the CAR-T lymphocytes transduced with the improved LV-CD9-BBz(86) is much lower than that by the CAR-T lymphocytes transduced with LV-CD9-BBz of the prior art under the co-culture with CD19-positive Raji tumor cells. The CAR-T lymphocytes transduced with the improved LV-CD19-BBz(86) produced cytokines at the same concentration as that by the CAR-T lymphocytes transduced with LV-CD19-BBz of the prior art under the co-culture with non-CD19 specific anti-CD3 (FIG. 2B). The CAR-T lymphocytes transduced with blank vector LV-control (i.e., LV-control/NS) as a control produced an extremely low concentration of cytokines in the absence of CD19-positive Raji tumor cells and non-CD19 specific anti-CD3.

Figure 3:
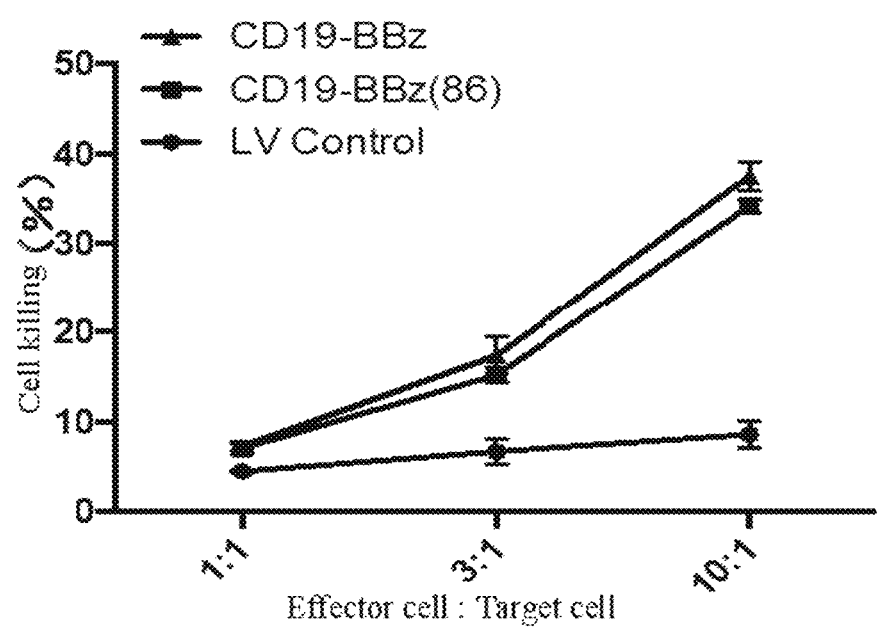
FIG. 3 is a graph showing the cell killing on CD19+ tumor cells by anti-CD19 CAR-T cells transduced with various recombinant lentiviral vectors according to embodiments of the present disclosure.

Example 4 Strong Tumor Cell Killing Ability of the Improved LV-CD9-BBz (86) CAR-T Lymphocyte In this example, peripheral blood lymphocytes taken from anonymous donors were separated by gradient centrifugation using the gradient centrifuge Ficoll-Hypaque. The T lymphocytes and T lymphocyte activating magnetic beads coated with monoclonal antibodies against CD3/CD28 (purchased from INVITROGEN, Carlsbad, Calif.) were incubated in the advanced RPMI medium 1640 with 2 mmol/L glutamine, 10% high-temperature inactivated fetal calf serum (FCS) (purchased from Sigma-Aldrich Co.) and 100 U/ml penicillin/streptomycin (purchased from INVITROGEN GIBCO, Cat. no. 12633-012) at 5% $CO_2$ and 37° C. for 72 hours. After activation and culturing for 72 hours, the T cells were washed with the washing buffer to remove the magnetic beads. The washed T cells were inoculated to cell culture dishes coated with recombinant fibronectin fragments (FN ch-296, RETRONECTIN). After that, the T cells were transduced with lentiviruses of the improved LV-CD19-BBz (86), LV-CD19-BBz of the prior art, or blank vector LV-control, which was conducted as described in Example 1. The transduced T cells were cultured in the RPMI-1640 medium and induced with recombinant human IL-2 factor (100 ng/ml, purchased from R&D SYSTEMS) for 7-10 days for amplification, and then were subjected to functional test experiments. The inventors measured the tumor cell killing ability of T cells transduced with different lentiviruses on CD19-positive Raji tumor cells at different ratios of effector cells to target cells according to the standard 4-hour-$^{51}$Cr-release method as described in Example 1. The results in FIG. 3 showed that both the CAR-T lymphocytes transduced with improved LV-CD19-BBz(86) and the CAR-T lymphocytes transduced with LV-CD19-BBz as the effector cells can kill CD19-positive Raji tumor cells as the target cells significantly, whereas the T lymphocytes transduced with lentivirus expressing non-functional EGFR only (i.e., LV-control T lymphocytes) kills CD19-positive tumor cells slightly. These results showed that the CAR-T lymphocytes transduced with improved LV-CD9-BBz(86) still have a strong tumor cell killing ability despite producing cytokines at significantly lower concentrations.

Example 5 Anti-EGFR Antibody Effectively Kills the CAR-T Lymphocytes Co-Expressing Non-Functional EGFR and Anti-CD19 Chimeric Antigen Receptor In this example, peripheral blood lymphocytes taken from anonymous donors were separated by gradient centrifugation using the gradient centrifuge Ficoll-Hypaque. The T lymphocytes and T lymphocyte activating magnetic beads coated with monoclonal antibodies against CD3/CD28 (purchased from INVITROGEN, Carlsbad, Calif.) were incubated in the advanced RPMI medium 1640 with 2 mmol/L glutamine, 10% high-temperature inactivated fetal calf serum (FCS) (purchased from Sigma-Aldrich Co.) and 100 U/ml penicillin/streptomycin (purchased from INVITROGEN GIBCO, Cat. no. 12633-012) at 5% $CO_2$ and 37° C. for 72 hours. After activation and culturing for 72 hours, the T cells were washed with the washing buffer to remove the magnetic beads. The washed T cells were inoculated to cell culture dishes coated with recombinant fibronectin fragments (FN ch-296, RETRONECTIN). After that, the T cells were transduced with lentiviruses of the improved LV-CD19-BBz (86), LV-CD19-BBz of the prior art, or blank vector LV-control, which was conducted as described in Example 1. The transduced T cells expressing non-functional EGFR were stained with anti-EGFR antibody followed by isolated by the flow cytometry (i.e., Fluorescence activated Cell Sorting, FACS). The isolated T cells as the target cells were cultured in the RPMI-1640 medium and induced with recombinant human IL-2 factor (100 ng/ml, purchased from R&D SYSTEMS) for 7-10 days for amplification. The inventors measured the killing effect on the T cells transduced with different lentiviruses mediated by anti-EGFR antibody according to the standard 4-hour-$^{51}$Cr-release method for ADCC assay, which was conducted as described in Example 1. It is shown that the anti-EGFR antibody can effectively mediate the killing of T lymphocytes expressing non-functional EGFR, whereas the anti-EGFR antibody cannot mediate the killing of non-transduced T lymphocytes not expressing non-functional EGFR.

Example 6 Significantly Decreased Proliferation on CAR-T Lymphocytes Transduced with Improved LV-CD19-BBz (86)

The inventors tested the proliferation activity of the CAR-T lymphocytes transduced with improved LV-CD19-BBz (86). The peripheral blood lymphocytes isolated from a healthy human were activated with immunomagnetic beads coated with monoclonal antibodies against CD3/CD28 (THERMOFISHER SCIENTIFIC, Waltham, Mass.) overnight at a ratio of 1:1. After that, the activated T lymphocytes were transduced with lentiviruses of the improved LV-CD19-BBz (86) or LV-CD19-BBz of the prior art. The counting on T cells showed that the T lymphocytes transduced with improved LV-CD19-BBz (86) and the T lymphocytes transduced with LV-CD19-BBz proliferated at a similar rate over the time, indicating that the transduction with CD19-CAR did not affect the endogenous TCR signal transduction of T cells. Further, the inventors tested the proliferation of the transduced CAR-T lymphocytes under antigen-specific cells. The inventors collected the transduced CAR-T cells, followed by removing the immunomagnetic beads and then co-cultured with irradiated CD19$^+$K562 cells at a ratio of 3:1. It is shown that the CAR-T lymphocytes transduced with improved LV-CD19-BBz (86) proliferated slower than the CAR-T lymphocytes transduced with LV-CD19-BBz, indicating that the CAR-T lymphocytes transduced with improved CD19-BBz (86) exhibited decreased cell proliferation.

Reference throughout this specification to "an embodiment", "some embodiments", "one embodiment", "another example", "an example", "a specific example" or "some examples" means that a particular feature, structure, material, or characteristic described in connection with the embodiment or example is included in at least one embodiment or example of the present disclosure. Thus, the appearances of the phrases of above-mentioned in various places throughout this specification are not necessarily referring to the same embodiment or example of the present disclosure. Furthermore, the particular features, structures, materials, or characteristics may be combined in any suitable manner in one or more embodiments or examples. In addition, those skilled in the art can combine the different embodiments or examples and the features of the different embodiments or examples described in the present specification without contradicting each other.

Although explanatory examples have been shown and described, it would be appreciated by those skilled in the art that the above examples cannot be construed to limit the present disclosure, and changes, alternatives, and modifications can be made in the examples without departing from spirit, principles and scope of the present disclosure.

What is claimed is:

1. A transgenic lymphocyte comprising:
   (i) a nucleic acid encoding a non-functional epidermal growth factor receptor (EGFR) and;
   (ii) a nucleic acid encoding an anti-CD19 chimeric antigen receptor (CAR), wherein the anti-CD19 CAR comprises:
   an extracellular segment, comprising a single-chain antibody region specifically binding to an antigen human CD19 and a hinge region,
   wherein the single-chain antibody region comprises a heavy chain variable region and a light chain variable region of the single-chain antibody, and the hinge region comprises an extracellular domain of human CD8 alpha (CD8α) of 55 amino acid residues and three alanine residues (AAA) located at the N-terminal of the extracellular domain of human CD8α, wherein the hinge region is of the amino acid sequence shown in SEQ ID NO: 7;
   a trans-membrane segment, comprising a trans-membrane domain of human CD8α linked to the hinge region of the extracellular segment and embedded in cell membrane of T lymphocyte, and
   an intracellular segment, comprising an intracellular domain of human CD8α, an intracellular domain of molecule 4-1BB and an intracellular domain of CD3 ζ chain,
   wherein the intracellular domain of human CD8α comprises seven amino acid residues and linked to the trans-membrane domain of human CD8α, wherein the intracellular domain of human CD8α is of the amino acid sequence as shown in SEQ ID NO: 3,
   and wherein the anti-CD19 CAR comprises SEQ ID NO: 8.

2. The transgenic lymphocyte according to claim 1, wherein the intracellular segment further comprises at least one intracellular domain of immune co-stimulation molecule selected from OX-40, CD40L, CD27, CD30, CD28 and derivatives thereof.

3. The transgenic lymphocyte according to claim 1, wherein the transgenic lymphocyte is a CD8+ T lymphocyte.

4. The transgenic lymphocyte according to claim 1, wherein the transgenic lymphocyte is a cytotoxic T-cell,
wherein the transgenic lymphocyte is comprises a natural killer (NK) cell or a natural killer T (NKT) cell.

5. The transgenic lymphocyte according to claim 1, wherein the chimeric antigen receptor and the non-functional EGFR are in a non-fused form.

6. The transgenic lymphocyte according to claim 1, wherein the transgenic lymphocyte is prepared by
introducing a lentivirus expressing the chimeric antigen receptor and the non-functional EGFR into a T lymphocyte, or
introducing a construct encoding the chimeric antigen receptor and the non-functional EGFR into a T lymphocyte.

7. The transgenic lymphocyte according to claim 6, wherein the lentivirus carries:
a first nucleic acid molecule, encoding the chimeric antigen receptor, wherein the chimeric antigen receptor comprises the amino acid sequence shown in SEQ ID NO: 8 and the first nucleic acid molecule comprises the nucleotide sequence shown in SEQ ID NO: 9, and
a second nucleic acid molecule, encoding the non-functional EGFR, wherein the non-functional EGFR comprises the amino acid sequence shown in SEQ ID NO: 10 and the second nucleic acid molecule comprises the nucleotide sequence shown in SEQ ID NO: 11; or
the lentivirus comprises the nucleotide sequence shown in SEQ ID NO: 12.

8. The transgenic lymphocyte according to claim 6, wherein the construct comprises:
a first nucleic acid sequence encoding the chimeric antigen receptor, and
a second nucleic acid sequence encoding the non-functional EGFR, and
a third nucleic acid sequence provided between the first nucleic acid sequence and the second nucleic acid sequence and encoding a linker peptide, wherein the linker peptide is cleavable in a lymphocyte.

9. The transgenic lymphocyte according to claim 8, wherein the construct further comprises:
a first promoter, operably linked to the first nucleic acid sequence, and
a second promoter, operably linked to the second nucleic acid sequence.

10. The transgenic lymphocyte according to claim 8, wherein the construct further comprises:
an internal ribosome entry site provided between the first nucleic acid sequence and the second nucleic acid sequence,
wherein the internal ribosome entry site comprises the nucleotide sequence shown in SEQ ID NO: 13.

11. The transgenic lymphocyte according to claim 8, wherein a vector of the construct is a non-pathogenic viral vector, and
the viral vector is at least one selected from retroviral vector, lentiviral vector and adenovirus-related viral vector.

12. A therapeutic composition for treating a cancer comprising:
the transgenic lymphocyte of claim 1 and a pharmaceutically acceptable carrier, wherein a tumor cell of the cancer has a high expression of CD19.

13. The transgenic lymphocyte according to claim 1, wherein
the extracellular domain of human 8α comprises the amino acid sequence shown in SEQ ID NO: 1,
the trans-membrane domain of human CD8α comprises the amino acid sequence shown in SEQ ID NO: 2,
the extracellular segment comprises the amino acid sequence shown in SEQ ID NO: 4,
the trans-membrane segment comprises the amino acid sequence shown in SEQ ID NO: 5, and
the intracellular segment comprises the amino acid sequence shown in SEQ ID NO: 6.

14. The transgenic lymphocyte according to claim 1, wherein the non-functional EGFR comprises the amino acid sequence shown in SEQ ID NO: 10.

* * * * *

SEQUENCE LISTING

```
<160> NUMBER OF SEQ ID NOS: 17

<210> SEQ ID NO 1
<211> LENGTH: 55
<212> TYPE: PRT
<213> ORGANISM: Artificial Sequence
<220> FEATURE:
<223> OTHER INFORMATION: Amino acid sequence of extracellular domain of
      human CD8 molecule

<400> SEQUENCE: 1

Phe Val Pro Val Phe Leu Pro Ala Lys Pro Thr Thr Thr Pro Ala Pro
1               5                   10                  15

Arg Pro Pro Thr Pro Ala Pro Thr Ile Ala Ser Gln Pro Leu Ser Leu
            20                  25                  30

Arg Pro Glu Ala Cys Arg Pro Ala Ala Gly Gly Ala Val His Thr Arg
        35                  40                  45

Gly Leu Asp Phe Ala Cys Asp
    50                  55

<210> SEQ ID NO 2
<211> LENGTH: 21
<212> TYPE: PRT
<213> ORGANISM: Artificial Sequence
<220> FEATURE:
<223> OTHER INFORMATION: Amino acid sequence of trans-membrane domain of
      human CD8 molecule
```

<400> SEQUENCE: 2

Ile Tyr Ile Trp Ala Pro Leu Ala Gly Thr Cys Gly Val Leu Leu Leu
1               5                   10                  15

Ser Leu Val Ile Thr
            20

<210> SEQ ID NO 3
<211> LENGTH: 7
<212> TYPE: PRT
<213> ORGANISM: Artificial Sequence
<220> FEATURE:
<223> OTHER INFORMATION: Amino acid sequence of intracellular domain of
      human CD8 molecule

<400> SEQUENCE: 3

Leu Tyr Cys Asn His Arg Asn
1               5

<210> SEQ ID NO 4
<211> LENGTH: 325
<212> TYPE: PRT
<213> ORGANISM: Artificial Sequence
<220> FEATURE:
<223> OTHER INFORMATION: Amino acid sequence of extracellular segment

<400> SEQUENCE: 4

Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Ser Thr Ser Gly Ser Gly Lys Pro Gly Ser Gly Glu Gly Ser
    130                 135                 140

Thr Lys Gly Glu Val Lys Leu Gln Glu Ser Gly Pro Gly Leu Val Ala
145                 150                 155                 160

Pro Ser Gln Ser Leu Ser Val Thr Cys Thr Val Ser Gly Val Ser Leu
                165                 170                 175

Pro Asp Tyr Gly Val Ser Trp Ile Arg Gln Pro Pro Lys Gly Leu
            180                 185                 190

Glu Trp Leu Gly Val Ile Trp Gly Ser Glu Thr Thr Tyr Tyr Asn Ser
        195                 200                 205

Ala Leu Lys Ser Arg Leu Thr Ile Ile Lys Asp Asn Ser Lys Ser Gln
    210                 215                 220

Val Phe Leu Lys Met Asn Ser Leu Gln Thr Asp Asp Thr Ala Ile Tyr
225                 230                 235                 240

Tyr Cys Ala Lys His Tyr Tyr Tyr Gly Gly Ser Tyr Ala Met Asp Tyr

```
                        245                 250                 255
Trp Gly Gln Gly Thr Ser Val Thr Val Ser Ser Ala Ala Phe Val
            260                 265                 270

Pro Val Phe Leu Pro Ala Lys Pro Thr Thr Pro Ala Pro Arg Pro
            275                 280                 285

Pro Thr Pro Ala Pro Thr Ile Ala Ser Gln Pro Leu Ser Leu Arg Pro
            290                 295                 300

Glu Ala Cys Arg Pro Ala Ala Gly Gly Ala Val His Thr Arg Gly Leu
305                 310                 315                 320

Asp Phe Ala Cys Asp
                325

<210> SEQ ID NO 5
<211> LENGTH: 21
<212> TYPE: PRT
<213> ORGANISM: Artificial Sequence
<220> FEATURE:
<223> OTHER INFORMATION: Amino acid sequence of trans-membrane segment

<400> SEQUENCE: 5

Ile Tyr Ile Trp Ala Pro Leu Ala Gly Thr Cys Gly Val Leu Leu Leu
1               5                   10                  15

Ser Leu Val Ile Thr
            20

<210> SEQ ID NO 6
<211> LENGTH: 161
<212> TYPE: PRT
<213> ORGANISM: Artificial Sequence
<220> FEATURE:
<223> OTHER INFORMATION: Amino acid sequence of intracellular segment

<400> SEQUENCE: 6

Leu Tyr Cys Asn His Arg Asn Lys Arg Gly Arg Lys Lys Leu Leu Tyr
1               5                   10                  15

Ile Phe Lys Gln Pro Phe Met Arg Pro Val Gln Thr Thr Gln Glu Glu
            20                  25                  30

Asp Gly Cys Ser Cys Arg Phe Pro Glu Glu Glu Glu Gly Gly Cys Glu
            35                  40                  45

Leu Arg Val Lys Phe Ser Arg Ser Ala Asp Ala Pro Ala Tyr Gln Gln
        50                  55                  60

Gly Gln Asn Gln Leu Tyr Asn Glu Leu Asn Leu Gly Arg Arg Glu Glu
65                  70                  75                  80

Tyr Asp Val Leu Asp Lys Arg Arg Gly Arg Asp Pro Glu Met Gly Gly
                85                  90                  95

Lys Pro Arg Arg Lys Asn Pro Gln Glu Gly Leu Tyr Asn Glu Leu Gln
            100                 105                 110

Lys Asp Lys Met Ala Glu Ala Tyr Ser Glu Ile Gly Met Lys Gly Glu
        115                 120                 125

Arg Arg Arg Gly Lys Gly His Asp Gly Leu Tyr Gln Gly Leu Ser Thr
130                 135                 140

Ala Thr Lys Asp Thr Tyr Asp Ala Leu His Met Gln Ala Leu Pro Pro
145                 150                 155                 160

Arg

<210> SEQ ID NO 7
<211> LENGTH: 58
<212> TYPE: PRT
```

<213> ORGANISM: Artificial Sequence
<220> FEATURE:
<223> OTHER INFORMATION: Amino acid sequence of hinge region

<400> SEQUENCE: 7

```
Ala Ala Ala Phe Val Pro Val Phe Leu Pro Ala Lys Pro Thr Thr Thr
1               5                   10                  15

Pro Ala Pro Arg Pro Pro Thr Pro Ala Pro Thr Ile Ala Ser Gln Pro
            20                  25                  30

Leu Ser Leu Arg Pro Glu Ala Cys Arg Pro Ala Ala Gly Gly Ala Val
        35                  40                  45

His Thr Arg Gly Leu Asp Phe Ala Cys Asp
    50                  55
```

<210> SEQ ID NO 8
<211> LENGTH: 507
<212> TYPE: PRT
<213> ORGANISM: Artificial Sequence
<220> FEATURE:
<223> OTHER INFORMATION: Amino acid sequence of chimeric antigen receptor

<400> SEQUENCE: 8

```
Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Ser Thr Ser Gly Ser Gly Lys Pro Gly Ser Gly Glu Gly Ser
    130                 135                 140

Thr Lys Gly Glu Val Lys Leu Gln Glu Ser Gly Pro Gly Leu Val Ala
145                 150                 155                 160

Pro Ser Gln Ser Leu Ser Val Thr Cys Thr Val Ser Gly Val Ser Leu
                165                 170                 175

Pro Asp Tyr Gly Val Ser Trp Ile Arg Gln Pro Pro Arg Lys Gly Leu
            180                 185                 190

Glu Trp Leu Gly Val Ile Trp Gly Ser Glu Thr Thr Tyr Tyr Asn Ser
        195                 200                 205

Ala Leu Lys Ser Arg Leu Thr Ile Ile Lys Asp Asn Ser Lys Ser Gln
    210                 215                 220

Val Phe Leu Lys Met Asn Ser Leu Gln Thr Asp Asp Thr Ala Ile Tyr
225                 230                 235                 240

Tyr Cys Ala Lys His Tyr Tyr Tyr Gly Gly Ser Tyr Ala Met Asp Tyr
                245                 250                 255

Trp Gly Gln Gly Thr Ser Val Thr Val Ser Ser Ala Ala Ala Phe Val
            260                 265                 270
```

```
Pro Val Phe Leu Pro Ala Lys Pro Thr Thr Pro Ala Pro Arg Pro
        275                 280                 285

Pro Thr Pro Ala Pro Thr Ile Ala Ser Gln Pro Leu Ser Leu Arg Pro
    290                 295                 300

Glu Ala Cys Arg Pro Ala Ala Gly Gly Ala Val His Thr Arg Gly Leu
305                 310                 315                 320

Asp Phe Ala Cys Asp Ile Tyr Ile Trp Ala Pro Leu Ala Gly Thr Cys
                325                 330                 335

Gly Val Leu Leu Leu Ser Leu Val Ile Thr Leu Tyr Cys Asn His Arg
                340                 345                 350

Asn Lys Arg Gly Arg Lys Lys Leu Leu Tyr Ile Phe Lys Gln Pro Phe
            355                 360                 365

Met Arg Pro Val Gln Thr Thr Gln Glu Glu Asp Gly Cys Ser Cys Arg
370                 375                 380

Phe Pro Glu Glu Glu Glu Gly Gly Cys Glu Leu Arg Val Lys Phe Ser
385                 390                 395                 400

Arg Ser Ala Asp Ala Pro Ala Tyr Gln Gln Gly Gln Asn Gln Leu Tyr
                405                 410                 415

Asn Glu Leu Asn Leu Gly Arg Arg Glu Glu Tyr Asp Val Leu Asp Lys
            420                 425                 430

Arg Arg Gly Arg Asp Pro Glu Met Gly Gly Lys Pro Arg Arg Lys Asn
        435                 440                 445

Pro Gln Glu Gly Leu Tyr Asn Glu Leu Gln Lys Asp Lys Met Ala Glu
    450                 455                 460

Ala Tyr Ser Glu Ile Gly Met Lys Gly Glu Arg Arg Arg Gly Lys Gly
465                 470                 475                 480

His Asp Gly Leu Tyr Gln Gly Leu Ser Thr Ala Thr Lys Asp Thr Tyr
                485                 490                 495

Asp Ala Leu His Met Gln Ala Leu Pro Pro Arg
                500                 505

<210> SEQ ID NO 9
<211> LENGTH: 1524
<212> TYPE: DNA
<213> ORGANISM: Artificial Sequence
<220> FEATURE:
<223> OTHER INFORMATION: Nucleotide sequence of nucleic acid molecule
      encoding chimeric antigen receptor

<400> SEQUENCE: 9
atgcttctcc tggtgacaag ccttctgctc tgtgagttac cacacccagc attcctcctg      60
atcccagaca tccagatgac acagactaca tcctccctgt ctgcctctct gggagacaga     120
gtcaccatca gttgcagggc aagtcaggac attagtaaat atttaaattg gtatcagcag     180
aaaccagatg gaactgttaa actcctgatc taccatacat caagattaca ctcaggagtc     240
ccatcaaggt tcagtggcag tgggtctgga acagattatt ctctcaccat tagcaacctg     300
gagcaagaag atattgccac ttacttttgc caacagggta atacgcttcc gtacacgttc     360 ggaggggggga ctaagttgga aataacaggc tccacctctg atccggcaa gcccggatct     420 ggcgagggat ccaccaaggg cgaggtgaaa ctgcaggagt caggacctgg cctggtggcg     480
ccctcacaga gcctgtccgt cacatgcact gtctcagggg tctcattacc cgactatggt     540
gtaagctgga ttcgccagcc tccacgaaag gtctggagt ggctgggagt aatatggggt     600
agtgaaacca catactataa ttcagctctc aaatccagac tgaccatcat caaggacaac     660
```

```
tccaagagcc aagttttctt aaaaatgaac agtctgcaaa ctgatgacac agccatttac    720
tactgtgcca acattatta ctacggtggt agctatgcta tggactactg gggtcaagga    780
acctcagtca ccgtctcctc agcggccgca ttcgtgccgg tcttcctgcc agcgaagccc    840
accacgacgc cagcgccgcg accaccaaca ccggcgccca ccatcgcgtc gcagcccctg    900
tccctgcgcc cagaggcgtg ccggccagcg gcggggggcg cagtgcacac gagggggctg    960
gacttcgcct gtgatatcta catctgggcg cccttggccg ggacttgtgg ggtccttctc   1020
ctgtcactgg ttatcaccct ttactgcaac cacaggaaca aacggggcag aaagaaactc   1080
ctgtatatat tcaaacaacc atttatgaga ccagtacaaa ctactcaaga ggaagatggc   1140
tgtagctgcc gatttccaga agaagaagaa ggaggatgtg aactgagagt gaagttcagc   1200
aggagcgcag acgccccgc gtaccagcag ggccagaacc agctctataa cgagctcaat   1260
ctaggacgaa gagaggagta cgatgttttg gacaagagac gtggccggga ccctgagatg   1320
gggggaaagc cgagaaggaa gaaccctcag gaaggcctgt acaatgaact gcagaaagat   1380
aagatggcgg aggcctacag tgagattggg atgaaaggcg agcgccggag gggcaagggg   1440
cacgatggcc tttaccaggg tctcagtaca gccaccaagg acacctacga cgcccttcac   1500
atgcaggccc tgccccctcg ctaa                                          1524
```

<210> SEQ ID NO 10
<211> LENGTH: 360
<212> TYPE: PRT
<213> ORGANISM: Artificial Sequence
<220> FEATURE:
<223> OTHER INFORMATION: Amino acid sequence of nonfunctional EGFR

<400> SEQUENCE: 10

```
Met Ala Leu Pro Val Thr Ala Leu Leu Leu Pro Leu Ala Leu Leu Leu
1               5                   10                  15

His Ala Ala Arg Pro Gly Ser Arg Lys Val Cys Asn Gly Ile Gly Ile
            20                  25                  30

Gly Glu Phe Lys Asp Ser Leu Ser Ile Asn Ala Thr Asn Ile Lys His
        35                  40                  45

Phe Lys Asn Cys Thr Ser Ile Ser Gly Asp Leu His Ile Leu Pro Val
    50                  55                  60

Ala Phe Arg Gly Asp Ser Phe Thr His Thr Pro Pro Leu Asp Pro Gln
65                  70                  75                  80

Glu Leu Asp Ile Leu Lys Thr Val Lys Glu Ile Thr Gly Phe Leu Leu
                85                  90                  95

Ile Gln Ala Trp Pro Glu Asn Arg Thr Asp Leu His Ala Phe Glu Asn
            100                 105                 110

Leu Glu Ile Ile Arg Gly Arg Thr Lys Gln His Gly Gln Phe Ser Leu
        115                 120                 125

Ala Val Val Ser Leu Asn Ile Thr Ser Leu Gly Leu Arg Ser Leu Lys
    130                 135                 140

Glu Ile Ser Asp Gly Asp Val Ile Ile Ser Gly Asn Lys Asn Leu Cys
145                 150                 155                 160

Tyr Ala Asn Thr Ile Asn Trp Lys Lys Leu Phe Gly Thr Ser Gly Gln
                165                 170                 175

Lys Thr Lys Ile Ile Ser Asn Arg Gly Glu Asn Ser Cys Lys Ala Thr
            180                 185                 190

Gly Gln Val Cys His Ala Leu Cys Ser Pro Glu Gly Cys Trp Gly Pro
        195                 200                 205
```

Glu Pro Arg Asp Cys Val Ser Cys Arg Asn Val Ser Arg Gly Arg Glu
    210                 215                 220
Cys Val Asp Lys Cys Asn Leu Leu Glu Gly Glu Pro Arg Glu Phe Val
225                 230                 235                 240
Glu Asn Ser Glu Cys Ile Gln Cys His Pro Glu Cys Leu Pro Gln Ala
                245                 250                 255
Met Asn Ile Thr Cys Thr Gly Arg Gly Pro Asp Asn Cys Ile Gln Cys
            260                 265                 270
Ala His Tyr Ile Asp Gly Pro His Cys Val Lys Thr Cys Pro Ala Gly
        275                 280                 285
Val Met Gly Glu Asn Asn Thr Leu Val Trp Lys Tyr Ala Asp Ala Gly
    290                 295                 300
His Val Cys His Leu Cys His Pro Asn Cys Thr Tyr Gly Cys Thr Gly
305                 310                 315                 320
Pro Gly Leu Glu Gly Cys Pro Thr Asn Gly Pro Lys Ile Pro Ser Ile
                325                 330                 335
Ala Thr Gly Met Val Gly Ala Leu Leu Leu Leu Leu Val Val Ala Leu
            340                 345                 350
Gly Ile Gly Leu Phe Met Arg Arg
        355                 360

<210> SEQ ID NO 11
<211> LENGTH: 1083
<212> TYPE: DNA
<213> ORGANISM: Artificial Sequence
<220> FEATURE:
<223> OTHER INFORMATION: Nucleotide sequence of nucleic acid molecule
      encoding nonfunctional EGFR

<400> SEQUENCE: 11
atggctctgc cgtcaccgc tctgctgctg cctctggctc tgctgctgca cgccgcacgc      60
cctgggagtc gcaaagtctg taatgggatc ggcatcggcg agttcaagga cagcctgtcc    120
atcaacgcca ccaatatcaa gcactttaag aattgcacat ctatcagcgg cgacctgcac    180
atcctgccag tggccttccg gggcgattct tttacccaca cccccctct ggaccctcag     240 gagctggata tcctgaagac cgtgaaggag atcacaggct cctgctgat ccaggcctgg     300 cctgagaaca gaaccgatct gcacgccttt gagaatctgg agatcatccg gggcagaaca    360
aagcagcacg gccagttctc cctggccgtg gtgtctctga acatcaccag cctgggcctg    420
aggtccctga ggagatctc tgacggcgat gtgatcatct ccggcaacaa gaacctgtgc    480
tacgccaaca caatcaattg gaagaagctg tttggcacct tggccagaa gacaaagatc     540 atctctaacc ggggcgagaa tagctgcaag gcaaccggac aggtgtgcca cgcactgtgc    600
agcccagagg gatgttgggg cccagagcca cgggactgcg tgagctgtag aaacgtgtcc    660
aggggccgcg agtgcgtgga taagtgtaat ctgctggagg gcgagccaag ggagttcgtg    720
gagaactccg agtgcatcca gtgtcacccc gagtgcctgc ctcaggccat gaacatcacc    780
tgtacaggcc gcggccccga caattgcatc cagtgtgccc actatatcga tggccctcac    840
tgcgtgaaga cctgtccagc cggcgtgatg ggcgagaaca atacactggt gtggaagtac    900
gcagacgcag gacacgtgtg ccacctgtgc caccccaatt gcacctatgg ctgtacagga    960
ccaggcctgg agggatgccc aaccaacggc cctaagatcc aagcatcgc cacaggcatg   1020 gtggggggcac tgctgctgct gctggtggtg gctctgggga ttgggctgtt tatgagaagg   1080
taa                                                                1083

<210> SEQ ID NO 12
<211> LENGTH: 3256
<212> TYPE: DNA
<213> ORGANISM: Artificial Sequence
<220> FEATURE:
<223> OTHER INFORMATION: Nucleotide sequence of nucleic acid molecule carried by lentivirus

<400> SEQUENCE: 12

| | | | | | |
|---|---|---|---|---|---|
| atgcttctcc | tggtgacaag | ccttctgctc | tgtgagttac | cacacccagc | attcctcctg | 60 |
| atcccagaca | tccagatgac | acagactaca | tcctccctgt | ctgcctctct | gggagacaga | 120 |
| gtcaccatca | gttgcagggc | aagtcaggac | attagtaaat | atttaaattg | gtatcagcag | 180 |
| aaaccagatg | gaactgttaa | actcctgatc | taccatacat | caagattaca | ctcaggagtc | 240 |
| ccatcaaggt | tcagtggcag | tgggtctgga | acagattatt | ctctcaccat | tagcaacctg | 300 |
| gagcaagaag | atattgccac | ttacttttgc | caacaggta | atacgcttcc | gtacacgttc | 360 |
| ggaggggga | ctaagttgga | aataacaggc | tccacctctg | gatccggcaa | gcccggatct | 420 |
| ggcgagggat | ccaccaaggg | cgaggtgaaa | ctgcaggagt | caggacctgg | cctggtggcg | 480 |
| ccctcacaga | gcctgtccgt | cacatgcact | gtctcagggg | tctcattacc | cgactatggt | 540 |
| gtaagctgga | ttcgccagcc | tccacgaaag | ggtctggagt | ggctgggagt | aatatggggt | 600 |
| agtgaaacca | catactataa | ttcagctctc | aaatccagac | tgaccatcat | caaggacaac | 660 |
| tccaagagcc | aagttttctt | aaaaatgaac | agtctgcaaa | ctgatgacac | agccatttac | 720 |
| tactgtgcca | acattatta | ctacggtggt | agctatgcta | tggactactg | ggtcaagga | 780 |
| acctcagtca | ccgtctcctc | agcggccgca | ttcgtgccgg | tcttcctgcc | agcgaagccc | 840 |
| accacgacgc | cagcgccgcg | accaccaaca | ccggcgccca | ccatcgcgtc | gcagccctg | 900 |
| tccctgcgcc | cagaggcgtg | ccggccagcg | gcgggggcg | cagtgcacac | gagggggctg | 960 |
| gacttcgcct | gtgatatcta | catctggcg | cccttggccg | ggacttgtgg | ggtccttctc | 1020 |
| ctgtcactgg | ttatcaccct | ttactgcaac | cacaggaaca | acggggcag | aaagaaactc | 1080 |
| ctgtatatat | tcaaacaacc | atttatgaga | ccagtacaaa | ctactcaaga | ggaagatggc | 1140 |
| tgtagctgcc | gatttccaga | agaagaagaa | ggaggatgtg | aactgagagt | gaagttcagc | 1200 |
| aggagcgcag | acgcccccgc | gtaccagcag | ggccagaacc | agctctataa | cgagctcaat | 1260 |
| ctaggacgaa | gagaggagta | cgatgttttg | gacaagagac | gtggccggga | ccctgagatg | 1320 |
| ggggaaagc | cgagaaggaa | gaaccctcag | gaaggcctgt | acaatgaact | gcagaaagat | 1380 |
| aagatgcgg | aggcctacag | tgagattggg | atgaaaggcg | agcgccggag | gggcaagggg | 1440 |
| cacgatggcc | tttaccaggg | tctcagtaca | gccaccaagg | acacctacga | cgcccttcac | 1500 |
| atgcaggccc | tgccccctcg | ctaatcctac | tgcgtcgact | tcgaatttaa | atcggatccg | 1560 |
| cggccgcgcc | cctctcccte | ccccccccct | aacgttactg | gccgaagccg | cttggaataa | 1620 |
| ggccggtgtg | cgtttgtcta | tatgttattt | tccaccatat | tgccgtcttt | tggcaatgtg | 1680 |
| agggcccgga | aacctggccc | tgtcttcttg | acgagcattc | ctaggggtct | ttcccctctc | 1740 |
| gccaaaggaa | tgcaaggtct | gttgaatgtc | gtgaaggaag | cagttcctct | ggaagcttct | 1800 |
| tgaagacaaa | caacgtctgt | agcgaccctt | gcaggcagc | ggaaccccc | acctggcgac | 1860 |
| aggtgcctct | gcggccaaaa | gccacgtgta | agatacac | ctgcaaaggc | ggcacaaccc | 1920 |
| cagtgccacg | ttgtgagttg | gatagttgtg | gaaagagtca | aatggctctc | ctcaagcgta | 1980 |
| ttcaacaagg | ggctgaagga | tgcccagaag | gtaccccatt | gtatgggatc | tgatctgggg | 2040 |

```
cctcggtgca catgctttac atgtgtttag tcgaggttaa aaaaacgtct aggccccccg    2100
aaccacgggg acgtggtttt cctttgaaaa acacgatgat aatatggcca caaccatggc    2160
gtccggatct agaatggctc tgcccgtcac cgctctgctg ctgcctctgg ctctgctgct    2220
gcacgccgca cgcccggga gtcgcaaagt ctgtaatggg atcggcatcg gcgagttcaa    2280
ggacagcctg tccatcaacg ccaccaatat caagcacttt aagaattgca catctatcag    2340
cggcgacctg cacatcctgc cagtggcctt ccggggcgat tcttttaccc acacaccccc    2400
tctggaccct caggagctgg atatcctgaa gaccgtgaag gagatcacag gcttcctgct    2460
gatccaggcc tggcctgaga cagaaccga tctgcacgcc tttgagaatc tggagatcat    2520
ccggggcaga acaaagcagc acggccagtt ctccctggcc gtggtgtctc tgaacatcac    2580
cagcctgggc ctgaggtccc tgaaggagat ctctgacggc gatgtgatca tctccggcaa    2640
caagaacctg tgctacgcca acacaatcaa ttggaagaag ctgtttggca cctctggcca    2700
gaagacaaag atcatctcta accggggcga gaatagctgc aaggcaaccg gacaggtgtg    2760
ccacgcactg tgcagcccag agggatgttg ggggcccagag ccacgggact gcgtgagctg    2820
tagaaacgtg tccaggggcc gcgagtgcgt ggataagtgt aatctgctgg agggcgagcc    2880
aagggagttc gtggagaact ccgagtgcat ccagtgtcac cccgagtgcc tgcctcaggc    2940
catgaacatc acctgtacag gccgcggccc cgacaattgc atccagtgtg cccactatat    3000
cgatggccct cactgcgtga agacctgtcc agcggcgtg atgggcgaga caatacact    3060 ggtgtggaag tacgcagacg caggacacgt gtgccacctg tgccacccca attgcaccta    3120
tggctgtaca ggaccaggcc tggagggatg cccaaccaac ggccctaaga tcccaagcat    3180
cgccacaggc atggtggggg cactgctgct gctgctggtg gtggctctgg ggattgggct    3240
gtttatgaga aggtaa                                                   3256

<210> SEQ ID NO 13
<211> LENGTH: 587
<212> TYPE: DNA
<213> ORGANISM: Artificial Sequence
<220> FEATURE:
<223> OTHER INFORMATION: Nucleotide sequence of internal ribosome entry
      site

<400> SEQUENCE: 13
cccctctccc tccccccccc ctaacgttac tggccgaagc cgcttggaat aaggccggtg      60
tgcgtttgtc tatatgttat tttccaccat attgccgtct tttggcaatg tgagggcccg     120
gaaacctggc cctgtcttct tgacgagcat tcctaggggt cttccctc tcgccaaagg      180 aatgcaaggt ctgttgaatg tcgtgaagga agcagttcct ctggaagctt cttgaagaca     240
aacaacgtct gtagcgaccc tttgcaggca gcggaacccc ccacctggcg acaggtgcct     300
ctgcggccaa aagccacgtg tataagatac acctgcaaag gcggcacaac cccagtgcca     360
cgttgtgagt tggatagttg tggaaagagt caaatggctc tcctcaagcg tattcaacaa     420
ggggctgaag gatgcccaga aggtacccca ttgtatggga tctgatctgg ggcctcggtg     480
cacatgcttt acatgtgttt agtcgaggtt aaaaaaacgt ctaggccccc cgaaccacgg     540
ggacgtggtt ttcctttgaa aaacacgatg ataatatggc cacaacc                   587

<210> SEQ ID NO 14
<211> LENGTH: 18
<212> TYPE: PRT
<213> ORGANISM: Artificial Sequence
<220> FEATURE:
```

```
<223> OTHER INFORMATION: Amino acid sequence of linker peptide

<400> SEQUENCE: 14

Glu Gly Arg Gly Ser Leu Leu Thr Cys Gly Asp Val Glu Glu Asn Pro
1               5                   10                  15

Gly Pro

<210> SEQ ID NO 15
<211> LENGTH: 19
<212> TYPE: PRT
<213> ORGANISM: Artificial Sequence
<220> FEATURE:
<223> OTHER INFORMATION: Amino acid sequence of linker peptide

<400> SEQUENCE: 15

Ala Thr Asn Phe Ser Leu Leu Lys Gln Ala Gly Asp Val Glu Glu Asn
1               5                   10                  15

Pro Gly Pro

<210> SEQ ID NO 16
<211> LENGTH: 20
<212> TYPE: PRT
<213> ORGANISM: Artificial Sequence
<220> FEATURE:
<223> OTHER INFORMATION: Amino acid sequence of linker peptide

<400> SEQUENCE: 16

Gln Cys Thr Asn Tyr Ala Leu Leu Lys Leu Ala Gly Asp Val Glu Ser
1               5                   10                  15

Asn Pro Gly Pro
            20

<210> SEQ ID NO 17
<211> LENGTH: 22
<212> TYPE: PRT
<213> ORGANISM: Artificial Sequence
<220> FEATURE:
<223> OTHER INFORMATION: Amino acid sequence of linker peptide

<400> SEQUENCE: 17

Val Lys Gln Thr Leu Asn Phe Asp Leu Leu Lys Leu Ala Gly Asp Val
1               5                   10                  15

Glu Ser Asn Pro Gly Pro
            20
```